US009408823B2

(12) United States Patent
Nelson et al.

(10) Patent No.: US 9,408,823 B2
(45) Date of Patent: *Aug. 9, 2016

(54) BENZONATATE MODIFIED RELEASE SOLID TABLETS AND CAPSULES

(71) Applicant: TRIS Pharma Inc., Monmouth Junction, NJ (US)

(72) Inventors: Andrea Nelson, Edison, NJ (US); Quin-Zene Chen, Belle Mead, NJ (US); Harsh Mehta, Monroe Township, NJ (US); Yu-Hsing Tu, West Windsor, NJ (US)

(73) Assignee: Tris Pharma, Inc., Monmouth Junction, NJ (US)

(*) Notice: Subject to any disclaimer, the term of this patent is extended or adjusted under 35 U.S.C. 154(b) by 19 days.

This patent is subject to a terminal disclaimer.

(21) Appl. No.: 14/863,784

(22) Filed: Sep. 24, 2015

(65) Prior Publication Data

US 2016/0008312 A1    Jan. 14, 2016

Related U.S. Application Data

(63) Continuation of application No. 14/282,058, filed on May 20, 2014, now Pat. No. 9,180,104, which is a continuation of application No. PCT/US2014/023106, filed on Mar. 11, 2014.

(60) Provisional application No. 61/872,019, filed on Aug. 30, 2013, provisional application No. 61/780,689, filed on Mar. 13, 2013.

(51) Int. Cl.
| | |
|---|---|
| *A61K 9/22* | (2006.01) |
| *A61K 31/245* | (2006.01) |
| *A61K 31/09* | (2006.01) |
| *A61K 9/24* | (2006.01) |
| *A61K 9/28* | (2006.01) |
| *A61K 45/06* | (2006.01) |
| *A61K 9/00* | (2006.01) |
| *A61K 9/20* | (2006.01) |
| *A61K 9/50* | (2006.01) |

(52) U.S. Cl.
CPC ............. *A61K 31/245* (2013.01); *A61K 9/0053* (2013.01); *A61K 9/209* (2013.01); *A61K 9/2009* (2013.01); *A61K 9/2054* (2013.01); *A61K 9/2077* (2013.01); *A61K 9/2081* (2013.01); *A61K 9/2846* (2013.01); *A61K 9/2866* (2013.01); *A61K 9/2886* (2013.01); *A61K 31/09* (2013.01); *A61K 45/06* (2013.01); *A61K 9/2013* (2013.01); *A61K 9/5084* (2013.01)

(58) Field of Classification Search
CPC ..... A61K 9/2013; A61K 9/254; A61K 9/251; A61K 9/209; A61K 9/5054; A61K 31/09; A61K 31/245

USPC ................................................ 424/464–489
See application file for complete search history.

(56) References Cited

U.S. PATENT DOCUMENTS

| | | | |
|---|---|---|---|
| 4,775,694 A | 10/1988 | Press et al. | |
| 4,915,948 A | 4/1990 | Gallopo et al. | |
| 5,401,512 A | 3/1995 | Rhodes et al. | |
| 6,423,339 B1 | 7/2002 | Spireas | |
| 6,793,934 B1 * | 9/2004 | Burnside ................ | A61K 9/143 424/400 |
| 7,148,211 B2 | 12/2006 | Mazess et al. | |
| 8,062,667 B2 | 11/2011 | Mehta et al. | |
| 8,202,537 B2 | 6/2012 | Mehta et al. | |
| 8,202,542 B1 | 6/2012 | Mehta et al. | |
| 8,287,848 B2 | 10/2012 | Mehta et al. | |
| 8,287,903 B2 | 10/2012 | Mehta et al. | |
| 8,337,890 B2 | 12/2012 | Mehta et al. | |
| 8,357,398 B2 | 1/2013 | Howard et al. | |
| 8,465,765 B2 | 6/2013 | Mehta et al. | |
| 8,491,935 B2 | 7/2013 | Mehta et al. | |
| 8,512,688 B2 | 8/2013 | Mehta et al. | |
| 8,563,033 B1 | 10/2013 | Mehta et al. | |
| 8,597,684 B2 | 12/2013 | Mehta et al. | |
| 8,623,409 B1 | 1/2014 | Mehta et al. | |
| 2004/0265372 A1 | 12/2004 | Wynn et al. | |
| 2005/0137372 A1 | 6/2005 | Kulkarni et al. | |
| 2006/0141031 A1 | 6/2006 | Nelson et al. | |

(Continued)

FOREIGN PATENT DOCUMENTS

| | | |
|---|---|---|
| WO | WO 01/41737 A2 | 6/2001 |
| WO | WO 04/000273 A1 | 12/2003 |
| WO | WO 2008/089260 A2 | 7/2008 |
| WO | WO 2012/054067 A1 | 4/2012 |

OTHER PUBLICATIONS

J.M. Huber Corporation, Zeopharm® 600 Product Specifications, revised Jun. 28, 2010.
BASF SE, "Benzonatate", Pharma Active Ingredients web page, http://product-finder.basf.com/group/corporate/product-finder/en/brand/BENZONATATE, accessed Dec. 19, 2014.
Evans et al., "Measurement of gastrointestinal pH profiles in normal ambulant human subjects", Gut, vol. 29(8):1035-1041, Aug. 1988.
Pfizer Inc., Tessalon®, 100 mg Perles 200 mg Capsules (Product Literature), revised Dec. 2015.

(Continued)

*Primary Examiner* — Micah-Paul Young
(74) *Attorney, Agent, or Firm* — Howson and Howson LLP; Egon Berg, Esq.; Cathy A. Kodroff

(57) ABSTRACT

A 12-hour anti-tussive modified release solid tablet or capsule is described which comprises a benzonatate adsorbate in a matrix with a sufficient amount of one or more pharmaceutically acceptable modified release pH-independent, substances to provide a 12-hour modified release profile to the benzonatate, wherein there is substantially no benzonatate release from the tablet or capsule in the buccal cavity and no more than about 25% release of the benzonatate within 1 hour as determined in an in vitro dissolution assay.

21 Claims, 1 Drawing Sheet

(56) References Cited

U.S. PATENT DOCUMENTS

| | | |
|---|---|---|
| 2006/0182796 A1 | 8/2006 | Wu et al. |
| 2006/0222700 A1 | 10/2006 | Groenewoud |
| 2007/0048371 A1 | 3/2007 | Shojaei et al. |
| 2008/0176955 A1 | 7/2008 | Heck et al. |
| 2009/0169583 A1 | 7/2009 | Brodeur et al. |
| 2010/0087501 A1 | 4/2010 | Mehta et al. |
| 2011/0091509 A1 | 4/2011 | Howard et al. |
| 2012/0148672 A1 | 6/2012 | Mehta et al. |
| 2013/0096191 A1 | 4/2013 | Howard et al. |
| 2014/0004160 A1 | 1/2014 | Mehta et al. |
| 2014/0030334 A1 | 1/2014 | Mehta et al. |
| 2014/0056984 A1 | 2/2014 | Mehta et al. |
| 2014/0093578 A1 | 4/2014 | Mehta et al. |
| 2014/0127306 A1 | 5/2014 | Mehta et al. |

OTHER PUBLICATIONS

International Search Report and Written Opinion, dated May 30, 2014, issued in International Patent Application No. PCT/US2014/023106.

medicinenet.com, "Benzonatate, Tessalon Perles; Zonatuss", Feb. 20, 2015, retrieved from www.medicinenet.com/benzonatate/article.html on May 21, 2014.

medicalook.com, "Benzonatate review", retrieved from http://www.medicalook.com/reviews/benzonatate.html, on May 21, 2014.

* cited by examiner

BENZONATATE MODIFIED RELEASE SOLID TABLETS AND CAPSULES

CROSS-REFERENCE TO RELATED APPLICATIONS

This is a continuation of U.S. patent application Ser. No. 14/282,058, filed May 20, 2014, which is a continuation of PCT/US14/23106, filed Mar. 11, 2014, which claims the benefit of the priority of U.S. Provisional Patent Application No. 61/872,019, filed Aug. 30, 2013, and U.S. Provisional Patent Application No. 61/780,689, filed Mar. 13, 2013, now expired, all of which are incorporated herein by reference.

BACKGROUND OF THE INVENTION

Benzonatate is a non-narcotic oral cough suppressant, or antitussive, with therapeutic effects that last about 6 to 8 hours following delivery of an immediate release composition. Its formal name is 2,5,8,11,14,17,20,23,26-nonaoxaoctacosan-28-yl para-butylaminobenzoate. Since it is not an opioid, benzonatate is not prone to potential abuse like some other cough medications such as codeine. See, e.g., U.S. Pat. No. 8,357,398. Benzonatate was approved by the U.S. Food and Drug Administration (FDA) in 1958 for administration as an anti-tussive. [www.medicinenet.com/Benzonatate/article-.htm, accessed on Mar. 12, 2013].

Benzonatate is a butylamine, chemically related to other ester local anesthetics such as procaine and tetracaine. Benzonatate is reported to act as a local anesthetic, decreasing the sensitivity of stretch receptors in the lower airway and lung, thereby reducing the drive to cough after taking a deep breath. See, e.g., U.S. Pat. No. 4,775,694. As an antitussive, benzonatate is reported to reduce coughing in various respiratory conditions such as bronchitis, emphysema, influenza, and pneumonia. See, e.g., http://www.medicalook.com/reviews/Benzonatate.html, accessed on Mar. 12, 2013.

U.S. Pat. No. 8,357,398, WO 2012/054067, US 2013/0096191A1, US 2011/0091509, all Howard et al, describe oral doses forms of benzonatate stated to be useful for anti-tussive applications. Howard et al, describe binding benzonatate to an ion exchange resin for the described purposes of reducing the choking hazard and noxious taste of benzonatate.

U.S. Pat. No. 6,793,934, Burnside et al, describe the use of granulated magnesium aluminometalsilicate alone, or together with dibasic calcium phosphate, to convert a liquid drug such as benzonatate to a powder. The '934 patent describes mixing benzonatate with ethyl alcohol to reduce its viscosity prior to blending with the combination of granulated magnesium aluminometalsilicate and dibasic calcium phosphate, and magnesium stearate. The ethyl alcohol is removed during processing of the resulting powder.

U.S. Pat. No. 4,775,694, Press et al, claim an oil-in-water emulsion with a continuous water phase and a discontinuous oil phase. Essentially all of the benzonatate is present in the discontinuous oil phase of the emulsion.

US Application No. 2008/0176955 A1, Heck et al, describe pharmaceutical compositions containing a combination of benzonatate and guaifenesin which are designed to provide cough relief to opiate-sensitive individuals, including infants and other pediatric patents.

Benzonatate is currently commercially available in immediate release form as 100 mg and 200 mg softgel capsules. Initial dose is one 100 mg gelcap by mouth, 3 times a day (8 hour effect). Dosage may be increased as necessary, up to a maximum of 600 mg per day. Due to its potency and potential toxicity, the capsules must be swallowed intact in order to allow slower release of the medication. Excessive absorption of benzonatate (a local anesthetic) in the oral mucosa will result in the rapid development of numbness of the mouth and throat. In extreme cases, the mouth and pharynx may become so numb that pulmonary aspiration may occur. Excessive absorption of benzonatate can occur if the gelcaps are chewed or allowed to dissolve in the mouth. This may lead to an overdose of the drug.

What is needed in the art are benzonatate compositions which avoid the undesirable side effects associated with release of this drug in the buccal cavity.

SUMMARY OF THE INVENTION

Modified release benzonatate solid compositions are described herein. By reducing the number of doses which are taken daily, the compositions herein provide added benefits, including convenience, for the patient. In addition, the compositions provided herein avoid release in the buccal cavity and provide a modified release of the benzonatate to reduce the number of doses required by day, thereby avoiding undesirable and potentially serious side effects associated with benzonatate. Additionally, it is an objective of the compositions provided herein is to provide a stable in vitro and in vivo release rate over at least the duration of conventional shelf-life storage conditions and times.

In one aspect, a modified release solid oral composition is provided which comprises (a) benzonatate in a matrix, wherein said matrix is a homogenous solid dispersion comprising (i) a benzonatate component and (ii) at least one pharmaceutically acceptable modified release pH-independent, hydrophilic or hydrophobic matrix-forming substance in an amount effective to provide a modified release profile to the benzonatate, and (b) a reverse enteric coating over the benzonatate in a matrix (a), wherein there is no more than about 50%, preferably less than about 40%, more preferably less than about 25%, of the benzonatate released from the composition within 1 hour, about 50% to about 80% of the benzonatate release from the composition within about 6 hours, and not less than about 80% released from the composition at about 12 hours, as determined in an in vitro dissolution test and substantially no benzonatate release from the composition in the buccal cavity or esophagus.

In another aspect, an anti-tussive modified release solid tablet or capsule composition is provided which comprises benzonatate in a matrix, wherein said matrix is a homogenous solid dispersion comprising (a) a benzonatate component selected from the group consisting of (i) an adsorbate comprising benzonatate and an adsorbent or (ii) a benzonatate-weak acidic ion exchange resin complex and (b) at least one pharmaceutically acceptable modified release pH-independent, high melt temperature, matrix-forming water-insoluble wax or waxy substance in an amount effective to provide a modified release profile to the benzonatate, wherein there is no more than about 50% release of the benzonatate from the composition within 1 hour as determined in an in vitro dissolution assay and substantially no benzonatate release from the composition in the buccal cavity or esophagus. In one embodiment, the benzonatate adsorbate comprises benzonatate and a silica or silicate. One suitable example of a silicate is calcium silicate.

In a further aspect, an anti-tussive modified release solid tablet or capsule composition is described which comprises benzonatate in a matrix, wherein said matrix is a homogenous solid dispersion comprising (a) an adsorbate comprising a benzonatate and a nonmetallic based silica and (b) about 5% w/w to about 30% w/w glyceryl behenate, wherein there is no more than about 25% release of the benzonatate from the composition within 1 hour as determined in an in vitro dissolution assay and substantially no benzonatate release from the composition in the buccal cavity or esophagus.

In still a further aspect, an anti-tussive modified release solid tablet is described which comprises a homogenous dispersion comprising benzonatate-calcium silicate adsorbate and at least one pharmaceutically acceptable modified release pH-independent, high melt temperature, matrix-forming water-insoluble wax or waxy substance in an amount effective to provide a modified release profile to the benzonatate, wherein there is no more than about 25% release of the benzonatate within 1 hour as determined in an in vitro dissolution assay and substantially no benzonatate release from the composition in the buccal cavity or esophagus.

In another aspect, an anti-tussive modified release solid oral tablet is described which comprises a core and a reverse enteric coating over said core. The core comprises benzonatate in a matrix, wherein said matrix is a homogenous solid dispersion comprising (a) an adsorbate comprising benzonatate and a silica, wherein the weight percentage of benzonatate in the adsorbate is about to 50% by weight benzonatate to about 75% by weight benzonatate, based on the weight of the adsorbate, (b) about 4% to about 20% of a hydrophilic or hydrophilic matrix forming material, by weight based on the weight of the core, and wherein the ratio of benzonatate adsorbate to polymer is about 8:1 to about 1:1, or ratios in between, e.g., about 6:1 to about 2:1. The tablet further comprises 5% to about 20% by weight of a reverse enteric coating wherein the coating weight percentage is based on the total coated tablet prior to any optional seal coat, wherein there is substantially no benzonatate release from the tablet in the buccal cavity or esophagus and no more than about 25% release of the benzonatate within 1 hour as determined in an in vitro dissolution assay.

In yet a further aspect, a 12-hour anti-tussive modified release solid tablet or capsule composition is described which comprises benzonatate in a matrix, wherein said matrix is a homogenous solid dispersion comprising (a) a benzonatate-weak acidic ion exchange resin complex and (b) at least one pharmaceutically acceptable modified release pH-independent, high melt temperature, matrix-forming water-insoluble wax or waxy substance in an amount effective to provide a 12-hour modified release profile to the benzonatate, wherein there is no more than about 25% release of the benzonatate within 1 hour as determined in an in vitro dissolution assay and substantially no benzonatate release from the composition in the buccal cavity or esophagus.

In still a further aspect, a 12-hour anti-tussive modified release solid composition comprising benzonatate is provided. This solid composition provides a pharmacokinetic profile for benzonatate in which its geometric mean maximum plasma concentration which has an area under the curve (AUC)inf of about 110 to about 170 ng-h/mL, a Cmax of about 15 to about 25 ng/mL and a Tmax of about 12 to 20 hours, following a daily oral administration of said solid composition (single dose equivalent to 300 mg benzonatate in adults/2×/day or 600 mg daily). In another embodiment, this composition provides an in vitro release, wherein there is no more than about 25% release of the benzonatate within 1 hour, not more than about 80% release within 6 hours, and not less than about 80% release at 12 hours, as determined in an in vitro dissolution assay and substantially no benzonatate release from the composition in the buccal cavity or esophagus.

In still a further aspect, a 12-hour anti-tussive modified release solid tablet or capsule comprising benzonatate is provided. This tablet or powder provides a pharmacokinetic profile for benzonatate in which its geometric mean maximum plasma concentration which has an area under the curve (AUC)inf of about 121 to about 245 ng-h/mL, a Cmax of about 28 to about 34 ng/mL and a Tmax of about 8 to 16 hours, following a daily oral administration of said solid composition (single dose equivalent to 300 mg benzonatate in adults, 2×/day (600 mg total/day).

Still other advantages and aspects of the invention will be readily apparent from the following detailed description of the invention.

DETAILED DESCRIPTION OF THE INVENTION

Figure 1A:
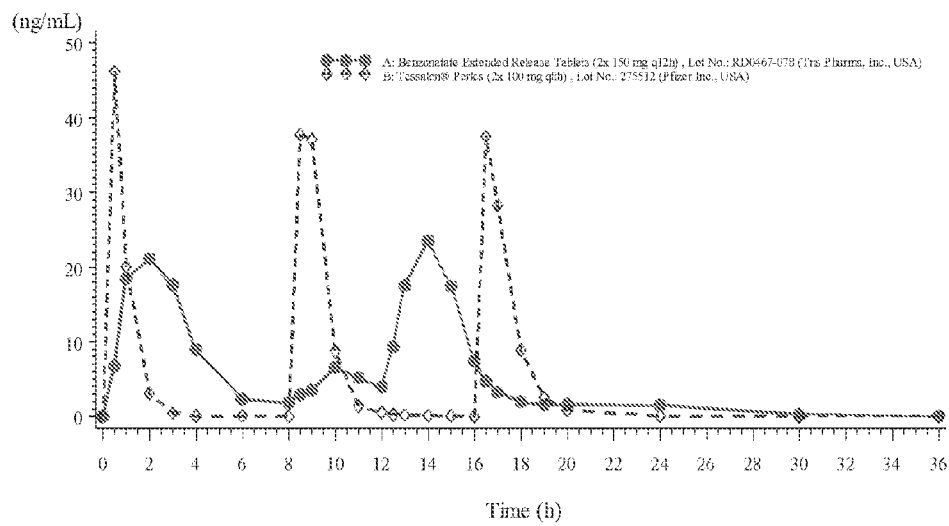
FIG. 1A is a graph providing the results of a biostudy comparing mean plasma benzonatate concentration-time profiles for a benzonatate extended release tablet (150 mg, administered 2×, q12h) as compared to a commercially available reference drug (Tessalon® Perles (2×100 mg q8h); Pfizer Inc). The number of subjects was 14. The test drug was administered at 0 and 12 hours and the reference drug were administered at 0, 8 and at 16 hours.

An anti-tussive modified release solid composition is provided which comprises a benzonatate component in a matrix which is a homogenous solid dispersion characterized by release of no more than about 55%, no more than about 50%, no more than about 40%, no more than about 30%, or no more than about 25% of the benzonatate from the composition, or release of less than 25% of the benzonatate in the composition within 1 hour as determined in an in vitro dissolution assay. In one embodiment, the matrix is formed upon admixture and/or compression of a benzonatate component with a modified release hydrophilic polymer or hydrophobic wax or waxy substance. The benzonatate component may be a solid benzonatate adsorbate or benzonate-ion exchange resin. The composition may have a reverse enteric coating. A modified release benzonatate solid composition provided herein is designed to avoid undesirable side effects associated with release of benzonatate in the buccal cavity and to provide stable in vitro and/or in vivo release profiles.

The solid compositions provided herein are may be a tablet, a powder-in-capsule, or mini-tabs loaded into a capsule.

As defined herein, a "stable" in vitro and/or in vivo release profile means that the in vitro dissolution profile and/or the in vivo pharmacokinetic profile of a modified release benzonatate solid composition described herein is the same or substantially the same following storage of the composition over a period of up to at least about 6 months, about 12 months, about 18 months, about 24 months under ambient conditions compared to when assessed substantially immediately following preparation of the composition. An in vitro dissolution release profile may be assessed using a suitable assay, such as those known to those of skill in the art or described herein. An in vivo pharmacokinetic profile of the composition may be assessed using parameters known in the art including, e.g., the area under the curve (AUC), Cmax, and Tmax. "Substantially the same" refers to a variance of less than about 5%, less than about 3%, or less than about 1%, between selected profile of the stored composition and the profile of the composition prior to storage.

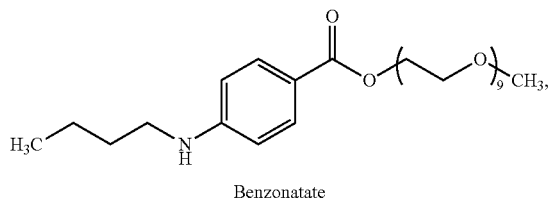

Benzonatate

The compound having the chemical name 2-[2-[2-[2-[2-[2-[2-[2-(2-methoxyethoxy) ethoxy]ethoxy]ethoxy]ethoxy]ethoxy]ethoxy]ethyl-4-butylaminobenzoate is commonly known as benzonatate. Benzonatate is pale yellow oily liquid at room temperature which is water soluble and moisture sensitive, but stable. Pharmaceutical grade benzonatate is commercially available, e.g., from BASF SE.

An immediate release benzonatate composition typically provides about a 6 to 8 hour effect (e.g., Tessalon®). Thus, a modified release benzonatate such as described herein is characterized by having therapeutically effective plasma levels of benzonatate for at least about 10 to at least about 12 hours following administration and up to about 24 hours.

The compositions described herein help to avoid an undesirable side effect associated with release of benzonatate in the buccal cavity or esophagus which side effects include temporary, potentially life-threatening local anesthesia of the oral mucosa, choking, or severe hypersensitivity reactions; oropharyngeal anesthesia can develop rapidly with improper administration. As used herein, the phrase "substantially no release of benzonatate" in the buccal cavity means that no amount of benzonatate and/or no amount of benzonatate which causes these side effects is released buccal cavity. As used herein, the term "buccal cavity" refers to the mouth, i.e., the area bounded by the lips, cheeks, and tongue.

A modified release solid composition comprising benzonatate is provided. In one embodiment, the composition provides a 12-hour tablet or capsule with a pharmacokinetic profile for benzonatate in which its geometric mean maximum plasma concentration which has an area under the curve (AUC)inf of about 110 to about 170 ng-h/mL, a Cmax of about 15 to about 25 ng/mL and a Tmax of about 12 to 20 hours, following a daily oral administration of benzonatate (single dose equivalent to 300 mg, 2×/day) in adults. In another embodiment, this composition provides an in vitro release, wherein there is no more than about 25% release of the benzonatate within 1 hour, no more than about 80% release within 6 hours, and not less than about 80% release at 12 hours, as determined in an in vitro dissolution assay and substantially no benzonatate release from the composition in the buccal cavity or esophagus.

In one embodiment, an anti-tussive modified release solid oral tablet or capsule composition contains benzonatate in a matrix. The matrix is a homogenous solid dispersion comprising a benzonatate component selected from the group consisting of (i) a dry, non-adherent, free-flowing compressible benzonatate adsorbate powder or (ii) a benzonatate-weak acidic cation exchange resin complex and (b) at least one pharmaceutically acceptable modified release pH-independent, matrix-forming hydrophilic polymer or hydrophobic high melt temperature, matrix-forming water-insoluble wax or waxy substance in an amount effective to provide a modified release profile to the benzonatate, characterized by release of no more than about 55%, no more than about 40%, no more than about 30%, or no more than about 25% of the benzonatate from the composition, or release of less than 25%, of the benzonatate in the composition within 1 hour. This release rate may be determined in an in vitro dissolution assay such as that described herein. In one embodiment, the adsorbate comprises a benzonatate and at least one adsorbent which is a nonmetallic based silica or silicate.

Figure 1B:
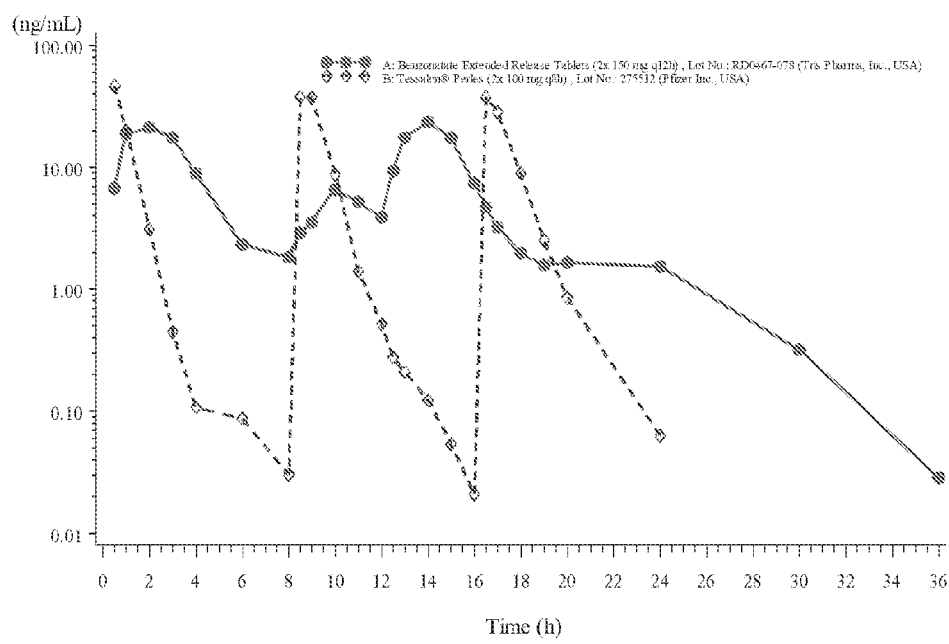
FIG. 1B is a graph providing the results of a biostudy comparing mean plasma benzonatate concentration-time profiles for a benzonatate extended release tablet (150 mg, administered 2×, q12h) as compared to a commercially available reference drug (Tessalon® Perles (2×100 mg q8h); Pfizer Inc). The number of subjects was 14. The test drug was administered at 0 and 12 hours and the reference drug were administered at 0, 12 and 16 hours.

In another embodiment, a 12-hour benzonatate modified release solid tablet or capsule comprising benzonatate is provided, in which the benzonatate has a pharmacokinetic profile of FIG. 1A or FIG. 1B at a dose equivalent to 300 mg daily dose of benzonatate (administered 2×/day, total daily equivalent to 600 mg benzonatate) in an adult. In another embodiment, the 12-hour benzonatate modified release solid tablet or capsule is characterized by providing benzonatate with a geometric mean maximum plasma concentration which has an area under the curve (AUC)inf of about 121 to about 245 ng-h/mL, a Cmax of about 28 to about 34 ng/mL and a Tmax of about 8 to 16 hours, following a single oral administration of said solid tablet at a dose equivalent to 300 mg benzonatate in adults. In one example, the tablet or capsule provides a benzonatate having a pharmacokinetic profile characterized by a geometric mean maximum plasma concentration which has an area under the curve (AUC)inf of about 150 ng-h/mL, a Cmax of about 30 ng/mL and a Tmax of about 12 hours.

As used herein, the "pH-independent, high melt temperature, matrix-forming, water-insoluble wax or waxy substance" includes hydrophobic waxes or wax-like substances which are solids at room temperature. While waxes having melting points in the range of about 30° C. to about 50° C. may be utilized, blending or other processing may need to be performed at cold temperatures to counter heat generated during processing for waxes or wax-like substances having lower melting points. Particularly desired are waxes and waxy-like substance which have melting point in the range of about 50° C. to about 80° C. Examples of a suitable pH-independent, high melt temperature, matrix-forming, water-insoluble wax or waxy substance include, e.g., stearyl alcohol, acetyl alcohol, glyceryl palmitostearte, glyceryl monostearate; and waxes selected from one or more of carnauba wax, beeswax, candelilla wax, microcrystalline wax, ozokerite wax, paraffin waxes, glyceryl behenate, glyceryl stearate, glyceryl oleate, glyceryl myristate, cetyl palmitate, cetyl caprate, stearyl palmitate, stearyl stearate, derivatives and mixtures thereof. In one embodiment, glyceryl behenate is used. Glyceryl behenate is available under the trade name of Compritol® 888 ATO (Gattefosse, France) has a melting point of approximately 70° C. and an HLB value of 2. In another embodiment, glyceryl palmitostearate or glyceryl behenate is used. The glyceryl palmitostearate under the trade name of Precirol® ATO 5 (Gattefosse, France) is a wax type lipid excipient with a melting point of approximately 56° C. and an HLB value of 2. In still another embodiment, cetostearyl alcohol is used, which has a melting point in the range of about 48° C. to about 56° C., or about 52° C. In a further examples, acetyl alcohol, which has a melting point in the range of about 45° C. to about 52° C. may be used alone or in combination with one or more waxes or waxy substance; Suitably, pharmaceutical grade waxes or waxy substances are used in the compositions.

As described herein, the amount of the at least one pH-independent, high melt temperature, matrix-forming, water-insoluble wax or waxy substance effective to provide the benzonatate with the 12-hour release profile described herein is generally in the amount of about 4% w/w to 60% w/w, about 4% w/w to about 20% w/w, or about 4% w/w to about 10% w/w of the at least one wax based on the weight of the total composition. Alternatively, the effective amount may be determined based on the ratio of the benzonatate adsorbate to the at least one wax, which is in the range of about 5:1 to about 2:1, or about 4:1 to about 3:1. In still another alternative, the effective amount of the matrix-forming wax may be determined based on the ratio of benzonatate-ion exchange resin complex to matrix-forming wax, which is in the range of about 5:1 to about 2:1, or about 3:1. These benzonatate modified release components are described in more detail in this specification.

As used herein, the "pH-independent, low viscosity, matrix-forming, modified release hydrophilic polymers" includes hydrophilic polymers which are solids at room temperature and which, when compressed into a matrix afford modified release properties to a drug within the matrix which is so formed. Suitable polymers may include natural gums, such as acacia gum tragacanth, locust bean gum, guar gum, karaya gum, modified celluloses, including methylcellulose, hydroxymethylcellulose (HMC), Hydroxypropyl cellulose (HPC), hydroxyethylcellulose, carboxymethylcellulose, Hydroxypropyl methylcellulose (hypromellose or HPMC), agar, pectin, carrageenan, alginate, carboxypolymethylene, gelatin, casein, and modified starch derivatives, or combinations thereof. A variety of food grade and pharmaceutical grade hydrophilic polymers are commercially available. For example, METHOCEL™ K-type Food Grade HPMCs, including, e.g., K100M, K15M, F4M, K4M, K100LV, K3, E15LV, E5 and E3. For purposes of illustration only, these may have average viscosities of about 4000 mPa-s (K4M), about 15,000 mPa-s (K15M), or about 100,000 mPa-S. One hydroxypropyl cellulose [LXF, Ashland Chemical] is characterized by a molecular weight of 95,000 and a viscosity of 75-150 mPa-S. Another illustrative HPC is characterized by a viscosity of 300 to 600 mPa-s and a molecular weight of about 80 kDa. Combinations of hydrophilic polymers may be utilized, including a combination of two or more hydrophilic polymers within the same class, but having different viscosities or molecular weights (e.g., two HPMCs), or two or more hydrophilic polymers of different classes (e.g., an HPC and an HPMC).

As described herein, the amount of the at least one pH-independent, matrix-forming, modified release hydrophilic polymer described herein is generally in a total amount of about 4% w/w to 60% w/w, about 4% w/w to about 20% w/w, or about 4% w/w to about 10% w/w of the at least one polymer based on the weight of the total composition. Alternatively, the effective amount may be determined based on the ratio of the benzonatate adsorbate to the at least one matrix-forming hydrophilic polymer, which is in the range of about 8:1 to about 1:1, or about 7:1 to about 5:1, or about 6:1. In still another alternative, the effective amount of the matrix-forming wax may be determined based on the ratio of benzonatate-ion exchange resin complex to matrix-forming wax, which is in the range of about 5:1 to about 2:1, or about 3:1. These benzonatate modified release components are described in more detail in this specification.

In still a further embodiment, a benzonatate composition may contain a combination of at least one modified release hydrophobic wax or wax-like substance and at least one hydrophilic modified release hydrophilic polymer. In such an embodiment, the combined total of hydrophobic wax or waxy-like substance and extended release matrix forming hydrophilic polymers is in the amount of about 4% w/w to 60% w/w, about 4% w/w to about 20% w/w, or about 4% w/w to about 10% w/w of the at least one wax based on the weight of the total composition. Alternatively, the effective amount may be determined based on the ratio of the benzonatate adsorbate to the at least hydrophobic or hydrophilic matrix forming polymer, which is in the range of about 8:1 to about 1:1, or about 4:1 to about 3:1.

The words "comprise", "comprises", and "comprising" are to be interpreted inclusively rather than exclusively. The works "consist", "consisting", and its variants, are to be interpreted exclusively, rather than inclusively.

As used herein in reference to numeric values provided herein, the term "about" may indicate a variability of as much as 10%.

Benzonatate Adsorbate

A modified release benzonatate composition is provided which contains solid dispersion comprising a benzonatate adsorbate in a matrix. Advantageously, by adsorbing the oily liquid benzonatate to an absorbent material such as described herein, the benzonatate becomes a powder composition, which reduces the risk associated with oropharyngeal side effects associated with buccal release of liquid benzonatate.

As used herein, the term "adsorbent" refers to a substance or carrier capable of attaching liquid benzonatate into a dry, non-adherent, free-flowing compressible powder. A powder is free flowing if it meets the processing characteristics such that in the process of making tablets the resulting tablet weights are uniform. Further, a powder is considered compressible if the resulting tablet with the hardness that can sustain <1% friability using USP test method.

Suitable adsorbents for the benzonatate are those with a relatively high adsorbency (loading) capacity for benzonatate and may be selected from calcium silicate (e.g., available as ZeoPharm® 600), silica, including precipitated amorphous silica (available as RxCipient GL100), and silicon dioxide (available as ZeoFree Plus 5193® 600). While lower amounts may be utilized, these adsorbents are capable of adsorbing as much as about 55%, or as much as about 60%, about 65% w/w, or up to about 70% w/w benzonatate. Other adsorbents may be selected from among, e.g., tricalcium phosphate (available as "Tri-tab" or tri-calcium phosphate DC) and bentonite (available as Bentonite Albagel Premium NF). These adsorbents generally have a maximum loading capacity in the range of about 30% w/w to about 40% w/w. However, it has been observed that when the tri-calcium phosphate is available or milled to a smaller particle size, its adsorbent (loading) capacity increases from a relative low capacity of about 20% w/w to about 25% w/w to an intermediate loading capacity of about 35% w/w to about 40% w/w. Thus, it is believed that milling the adsorbents with a low, or even an intermediate, loading capacity to a smaller particle size will increase adsorbency for benzonatate.

For example, the adsorbent materials have an average particle size of about 1 µm to about 500 µm. However, at the extreme low end of this range, the particles may exhibit greater lubricant properties and at the extreme upper end of this range, the larger particles may actually have lower surface area and thus lower loading capacities. Thus, particles are more typically selected from average particle size may be about 5 µm to about 200 µm, or about 10 µm to about 50 µm. However, particles in the range of up to about 325 microns, or up to about 420 microns may be used.

Calcium silicate, characterized by the formula $Ca_2SiO_4$, is particularly well suited for the compositions described herein because of its relatively high loading capacity and its ease of use during processing. Both the silicas and silicon dioxide tend to have flow properties similar to a lubricant, which may be detrimental during compression into a tablet and is a property not characteristic of calcium silicate. However, one or more of these components may be blended and that blend used as the adsorbent material. In one embodiment, magnesium or another alkali earth aluminometasilicate may be used alone or in combination with another of the adsorbents described herein. In another embodiment, aluminometasilicates are excluded from the compositions provided herein.

Examples of other adsorbates include, e.g., magnesium aluminometasilicate and dibasic calcium phosphate. Still other adsorbents include, e.g., microcrystalline cellulose, magnesium oxide, maltodextrins, bentonite, clay, celluloses, silicon dioxide, colloidal silicon dioxide, precipitated amorphous silica, kaolin, polyethylene glycol, talc, magnesium trisilicate, mono- or di-Calcium phosphate, tri-calcium phosphate, copovidone, montmorillonite, saponite, magnesium carbonate, calcium sulfate, magnesium stearate, calcium stearate, sodium stearate, stearic acid, Gelucire 44/14, Gelucire 50/13, Croscarmellose sodium, polyvinylpyrrolidone, cyclodextrins, gelatin, diatomite (kieselguhr), alginates, metal oxides.

In general, benzonatate is admixed (granulated) with one or more adsorbent materials as described herein to form a benzonatate adsorbate. For admixing, the benzonatate to adsorbent ratio is generally a ratio of about 5:1 to about 1:10, or about 4:1 to about 1:1, or about 3:1 to about 2:1, or about 2:1 to about 1:1. The benzonatate adsorbate may be prepared separately from formation of the matrix with the modified release, matrix forming hydrophobic or hydrophilic substance, or the adsorbate may be formed substantially simultaneously. For example, the liquid benzonatate may be admixed with water and the adsorbate material. Alternatively, benzonatate and the adsorbent material may be mixed together with at least one of the matrix-forming components. In the case of a wax, the component(s) is melted for a sufficient time to form the benzonatate adsorbate matrix. The melt temperature is generally in the range of about 50° C. to about 80° C., or about 55° C. to about 75° C., but may be lower or higher, taking into consideration the melt temperature of the wax(es) or waxy substance(s).

In order to facilitate production and even distribution of the adsorbate in the matrix, the benzonatate adsorbate powder granules are typically passed through a screen of about 10 mesh, which allows granules of less than about 2000 µm to pass through, or about 25 mesh, which allows granules of less than about 710 µm to pass through, about 30 mesh, which allows granules having an average size of less than about 590 µm to pass through, or about 40 mesh, which allows granules or particles having an average size of less than about 420 µm to pass through.

Where the benzonatate adsorbate is formed separately from the matrix, the benzonatate adsorbate may be admixed with the matrix-forming substance prior to adding any tableting excipients or other components (e.g., a pharmaceutically active ingredient in addition to benzonatate). Alternatively, the benzonatate adsorbate and the matrix-forming substance, as well as one or more excipients, and/or or an additional pharmaceutically active component, are combined at substantially the same time; in such case the matrix further comprises excipients and optional additional pharmaceutically active component. Still other production techniques may be designed by one of skill in the art in view of the information provided herein.

In order to facilitate processing, the benzonatate adsorbate-matrix granules may be passed through a screen of about 10 mesh, which allows granules or particles of less than about 2000 µm to pass through, about 25 mesh, which allows granules or particles of less than about 710 µm to pass through, about 30 mesh, which allows granules or particles having an average size of less than about 590 µm to pass through, or about 40 mesh, which allows granules or particles of about 420 µm to pass through.

In one embodiment, the benzonatate adsorbate comprises about 10% w/w to about 80% w/w benzonatate, about 20% w/w to about 70% w/w, about 50% w/w to about 70% w/w, about 50%, or about 25% to about 30% w/w benzonatate adsorbate (e.g., calcium silicate). In one example, the matrix comprising the benzonatate adsorbate comprises glyceryl behenate, wherein the ratio of benzonatate adsorbate to hydrophobic wax or waxy substance, hydrophobic polymer, or combinations thereof, are about 6:1 to about 2:1 or about 5:1 to about 4:1. Wherein the hydrophobic wax is glyceryl behenate, the ratio of benzonatate adsorbate to glyceryl behenate is about 6:1 to about 2:1, about 5:1 to about 4:1, or about 3.7:1 to about 3.4:1, based on weight in the composition. In another example, the matrix comprising the benzonatate-calcium silicate adsorbate comprises a combination of cetyl alcohol and stearyl alcohol. The ratio of cetyl alcohol to stearyl alcohol can be about 2:1 to about 1:2, or about 1.5:1 to about 1:1. When measured on the basis of the benzonatate alone, the weight ratio of benzonatate to the combined weight of cetyl alcohol and stearyl alcohol is about 5:1 to about 3:1. In one embodiment, the matrix comprises about 30% w/w benzonatate, about 3.5 to about 3.75% cetyl alcohol and about 4.25% to about 4.6% stearyl alcohol. In another embodiment, the matrix comprises the benzonatate-silicate adsorbate comprises cetyl alcohol, which is a fatty alcohol with the formula $CH_3(CH_2)_{15}OH$, also known as 1-Hexadecanol or palmityl alcohol. Pharmaceutical grade cetyl alcohol can be purchased, e.g., from Loba Chemie or Sigma Aldrich. In still another embodiment, the composition comprises a hydrophilic polymer and the ratio of benzonatate adsorbate to HPMC, HPC, or blends thereof, is about 2 parts by weight benzonatate adsorbate to about 0.5 to about 1 part by weight hydrophilic polymer(s), or about 0.7 to about 0.75 parts by weight HPMC (or HPC or blends thereof). In still a further embodiment, the composition comprising the benzonatate adsorbate comprises the hydrophilic polymer HPMC (or HPC or blends thereof), wherein the ratio of benzonatate adsorbate to HPMC (or HPC or blends thereof) is about 1 parts by weight benzonatate adsorbate to about 0.5 to about 1 part by weight HPMC (or HPC or blends thereof), or about 0.7 to about 0.75 parts by weight HPMC (or HPC or blends thereof). In yet another embodiment, the composition comprises a blend of hydrophobic wax/waxy like substances and hydrophilic polymers.

As described herein, a composition is a compressed tablet or a capsule composition. Such a composition may contain one or more excipients such as are described herein. In addition, a composition may further comprise one or more pharmaceutically active components in addition to the benzonatate. Such components are described in more detail elsewhere herein.

In one embodiment, a benzonatate tablet or powder composition as defined herein is characterized by having a pharmacokinetic profile as follows: a Cmax (arithmetic mean) of about 30 ng/mL to about 35 ng/mL, or about 33-33 ng/mL; a Cmax (geometric mean) of about 28 ng/mL to about 32 ng/mL, or about 30 ng/mL; an AUC inf (arithmetic mean) of about 180 to about 185 ng-h/mL, or about 182 ng-h/mL; an AUC inf (geometric mean) of about 145 ng-h/mL to about 155 ng-h/mL, or about 150 ng-h/mL; and Tmax of about 10 to about 15 hours, or about 12 hours, based on an equivalent of a single dose of about 300 mg benzonatate administered at 12 hour intervals (twice) in a 24 hour period (total daily dose about 600 mg benzonatate).

In another embodiment, a benzonatate tablet or powder composition as defined herein is characterized by having an in vitro profile as follows: At 0.5 hour, % release is about 15 to about 17% release, or about 16% release, at 1 hour, percent release is about 25 to about 28% release, or about 27% release, at 2 hours, percent release is about 42 to about 46% release, or about 44% release, at 3 hours, percent release is about 56 to about 65% release, or about 61% release, at 4 hours, percent release is about 75 to about 87% release, or about 82% release, at 6 hours, percent release is about 92 to about 99%, or about 97%, at 8 hours, percent benzonatate release is about 97 to about 99%, or about 99%, and at 12 hours, benzonatate release is about 98 to about 100% release, or about 100% release.

In still another embodiment, a 12-hour anti-tussive modified release solid composition comprising benzonatate provides a pharmacokinetic profile for benzonatate in which its geometric mean maximum plasma concentration which has an area under the curve (AUC)inf of about 110 to about 170 ng-h/mL, a Cmax of about 15 to about 25 ng/mL and a Tmax of about 12 to 20 hours, following a daily oral administration (2×/day) of a single dose equivalent to 300 mg benzonatate in adults (total equivalent to 600 mg/day). In another embodiment, a modified release benzonatate composition provides an in vitro release, wherein there is no more than about 50% release of the benzonatate within 1 hour, no more than about 50% to about 80% release within 6 hours, and no less than about 80% release at 12 hours, as determined in an in vitro dissolution assay and substantially no benzonatate release from the composition in the buccal cavity or esophagus. In another example, a benzonatate composition as described herein provides an in vitro release, wherein there is no more than about 40% release of the benzonatate within 1 hour, no more than about 50% to about 70% release within 6 hours, and no less than about 85% release at 12 hours, as determined in an in vitro dissolution assay and substantially no benzonatate release from the composition in the buccal cavity or esophagus. In still a further embodiment, a benzonatate composition provides an in vitro release, wherein there is no more than about 25% release of the benzonatate within 1 hour, not more than about 80% release within 6 hours, and not less than about 85% release at 12 hours, as determined in an in vitro dissolution assay and substantially no benzonatate release from the composition in the buccal cavity or esophagus. In still a further embodiment, this composition provides an in vitro release, wherein there is no more than about 15% to 20% release of the benzonatate within about 1 hour, no more than about 45 to 80% release within 6 hours, and not less than about 85% to about 99% release, as determined in an in vitro dissolution assay and substantially no benzonatate release from the composition in the buccal cavity or esophagus.

In one embodiment, this in vitro dissolution profile is that of the reverse enteric coated tablet comprising a benzonatate adsorbate. This may be assessed using the App (II) Paddle about 50 rpm, in a dissolution media of about 500 mL 0.1N HCl for about 1 hour, which is then adjusted to a pH of about 6.8 with a phosphate buffer, at a temperature of 37° C.

Benzonatate-Weak Acidic Cation Exchange Resin Complex

Although subject to a lower benzonatate loading capacity than the adsorbent materials described herein, the compositions described herein encompass a 12-hour anti-tussive modified release solid tablet or capsule which comprises a benzonatate-weak acidic ion exchange resin in a matrix with an effective amount of one or more pharmaceutically acceptable modified release pH-independent, high melt temperature, water-insoluble wax or waxy substances to provide a 12-hour modified release profile to the benzonatate.

Ion-exchange resins suitable for use in the compositions described herein are water-insoluble and comprise a preferably pharmacologically inert organic and/or inorganic matrix containing functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weak acidic (e.g., carboxylic acid), strongly basic (e.g., primary amine), weak basic (e.g. quaternary ammonium), or a combination of acidic and basic groups. Typically the size of the ion-exchange particles is from about 1 micron to about 900 microns, in another embodiment, about 5 microns to 750 microns, and in yet another embodiment, the particle size is within the range of about 40 microns to about 250 microns for liquid dosage forms although particles up to about 1,000 micron can be used for solid dosage forms, e.g., tablets and capsules. Resins are generally purchased with a size ranging from about 25 microns to about 400 microns. However, other sizes may be selected, or larger sized particles may be milled to provide smaller particle sizes.

Cationic exchange resins vary in strength, i.e., in their ability to exchange cations. A weak acidic ion exchange resin is well suited to prepare a benzonatate-ion exchange resin complex. An acid dissociation constant, pKa, (also known as acidity constant, or acid-ionization constant) is a quantitative measure of the strength of an acid in solution. The larger the value of pKa, the smaller the extent of dissociation. A strong acid such as $SO_3H$ pKa is approximately 0. A weak acid such COOH has pKa in the range of about 4 to about 7. Amberlite® IRP64 is thought to have pKa value of greater than 4 and is a weak acid resin (exchanging the H atom of the carboxylic acid (COOH) group). Amberlite® IRP64 (a methacrylic acid and divinylbenzene copolymer polyacrilex resin, Rohm and Haas, with a particle size ranging from 100 to 400 mesh (equiv to 35 microns to 150 microns, ASTM standard size), capacity ~10 meq/g by dry weight). Another weak cationic exchange resin may be selected, e.g., Amberlite® IRP88 [Rohm and Haas, a crosslinked co-polymer of methacrylic acid and divinylbenzene)], a weak acidic (potassium ion) cation exchange resin with 4% cross-linked methacrylate (100 to 500 mesh, equiv to about 150 microns to about 27 microns, ASTM standard). Either regularly or irregularly shaped particles may be used as cation exchange resins as described herein. Regularly shaped particles are those particles that substantially conform to geometric shapes such as spherical, elliptical, cylindrical and the like. Irregularly shaped particles are all particles not considered to be regularly shaped, such as particles with amorphous shapes and particles with increased surface areas due to surface channels or distortions.

Benzonatate may be complexed to the weak cation exchange resin using the methods described herein and those known in the art for loading or complexing other drugs to ion exchange resins. See, e.g., U.S. Pat. No. 8,062,667 and U.S. Pat. No. 8,337,890, which are incorporated by reference herein. Briefly, the benzonatate may be admixed with water prior to combining with the ion exchange resin or the ion exchange resin may be admixed with water separately or at the same time as being combined with the benzonatate in order to facilitate reaction and granulation. The benzonatate and weak cation exchange resin are admixed for a sufficient time in order to allow a benzonatate-weak acidic cation exchange resin complex to form. Typically, the benzonatate-weak acidic cation exchange resin complex is dried to a moisture content of less than about 10%, less than about 5%, or less than about 3%. The dried complex may be passed through a screen of a size no larger than about 40 mesh so that the complex particle size is less than about 420 microns. Suitably, the benzonatate-weak acid cation exchange resin complex is then admixed with the matrix-forming wax or waxy substance for a sufficient time to prepare a substantially homogenous solid dispersion. There optionally may be one or more excipients or pharmaceutical active ingredients in addition to the benzonatate included in the admixing stage and thus, in the matrix formed. The matrix-forming step and preparation of the final oral dosages unit may be performed using the same conditions as described for the benzonatate adsorbate.

In another embodiment, a benzonatate tablet or powder composition as defined herein is characterized by having an in vitro profile as follows: At 0.5 hr, % release is about 15 to about 17% release, or about 16% release, at 1 hour, percent release is about 25 to about 28% release, or about 27% release, at 2 hours, percent release is about 42 to about 46% release, or about 44% release, at 3 hours, percent release is about 56 to about 65% release, or about 61% release, at 4 hours, percent release is about 75 to about 87% release, or about 82% release, at 6 hours, percent release is about 92 to about 99%, or about 97%, at 8 hours, percent benzonatate release is about 97 to about 99%, or about 99%, and at 12 hours, benzonatate release is about 98 to about 100% release, or about 100% release. In one embodiment, this in vitro dissolution profile is a benzonatate-cation exchange resin complex in a matrix as defined herein.

Finishing Compositions Dosage Forms

A benzonatate composition as described herein may be a compressed tablet, which may be coated or optionally coated, or a capsule composition. Compressed tablets may be mini-tabs which are loaded into capsule shells or designed to be of a size for direct administration to a patient. Suitably, the solid compositions described herein are prepared as single uniform solid dispersion and are swallowed whole.

In addition to the compositions described herein where benzonatate is the single active ingredient, benzonatate composition may further comprise one or more pharmaceutically active components. Each of these additional active drugs may be independently in immediate release, modified release form, or both.

As previously described herein, a modified release benzonatate provides therapeutically effective benzonatate plasma levels over a period in excess of the immediate release benzonatate profile; which immediate release provides benzonatate for about 6 to 8 hours. Thus, a modified release composition provides an effective amount of benzonatate for at least about 10 hours to about 12 hours, up to about 24 hours. As used herein in connection with other pharmaceutically active drugs which may be combined with the benzonatate, the term "modified release" refers to compositions which provide effective amounts at least one of the active components (other than benzonatate) over a period of at least about 8 hours, and preferably up to about 24 hours. For a 24 hour release product, in one aspect, less than 50% of an active component is released at about 12 hours from administration. In another aspect, less than 60% of an active component is released at about 12 hours from administration. In still another aspect, less than 70% of an active component is released at about 12 hours. In still other embodiments, less than about 80% or more of an active component is released at about 12 hours. The term "modified release" may include, e.g., compositions which are extended release formulations, sustained release formulations, or delayed release formulations. The release profile may be assessed using in vitro dissolution assays known to those of skill in the art [e.g., USP basket method or Paddle Method, or channel flow method]. The release profile may be assessed in vivo (e.g., for bioavailability determinations), using plasma concentrations to assess maximum concentration (Cmax) and area under the curve (AUC). Such assays are well known to those of skill in the art.

By "immediate release", it is meant that the formulation containing the therapeutically active agent(s) meets the disintegration and/or dissolution requirements for immediate release of the particular therapeutically active agent(s), as set forth in the USP XXII, 1990 (The United States Pharmacopeia). Generally, the term "immediate release" is the release of an active ingredient from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time. In one embodiment for drugs other than benzonatate, immediate release provides for at least about 85% of the drug to be released in less than about one hour following administration to a patient and about 90% of the immediate release drug to be released in about 2 hours following administration to a patient. For example, a drug may release in about 10 minutes to about 45 minutes, or about 30 minutes. In another example, at least about 85%, at least about 90%, at least about 95%, or more, may be released within about 2 hours following administration to a patient.

Optionally, a benzonatate composition may contain an "immediate release benzonatate component". In one embodiment, a benzonatate composition as provided herein contains an immediate release benzonatate component in addition to the modified release benzonatate component. In one embodiment, the immediate release benzonatate is a benzonatate adsorbate or benzonatate-ion exchange resin complex which does not release benzonatate in the buccal cavity or esophagus, but releases immediately in the stomach and intestine. Such an immediate release benzonatate adsorbate or benzonatate-ion exchange resin complex may lack a hydrophilic or hydrophobic matrix forming material and further lacks any modified release and/or any reverse enteric coating layer. Suitably, such a composition contains about 5:1 to about 2.5:1 modified release to immediate release benzonatate component. In another embodiment, a benzonatate composition may contain a different pharmaceutically active component in immediate release form.

In order to combine an immediate release component into a benzonatate composition provided herein, the immediate release component could be applied as a separate layer in a bilayer tablet, e.g., homogenous dispersion comprising the benzonatate adsorbate-matrix forms a core and a top layer is an immediate release. Alternatively, the benzonatate adsorbate-matrix granules are admixed with an immediate release component and filled into a capsule. Still other methods of achieving this immediate release will be apparent to one of skill in the art given the guidance provided herein. Optionally, one or more additional active ingredients is admixed into the matrix and forms part of the homogenous dispersion formed with the benzonatate component and the matrix-forming wax. Alternatively, the one or more additional active ingredients is blended with the already formed benzonatate adsorbate-matrix or benzonatate-ion exchange resin complex-matrix and formed into the tablet. Still other methods of combining these additional active components into the tablet or capsule may be selected by one of skill in the art.

Particularly suitable classes of pharmaceutically active drugs for combination with the benzonatate include an antipyretic, an analgesic, an anti-histamine, an expectorant and a decongestant. Examples of suitable antipyretic analgesics include, e.g., sodium salicylate and salicyclic acid, non-steroidal anti-inflammatory drugs (NSAID), including ibuprofen, naproxen, aspirin, magnesium salicylate, diclofenac, etodolac, indomethacin, nabumetone, sulindac, tolmetin, ketoprofen, mefenamic acid, meclofenamic acid, phenylbutazone, piroxicam, meloxicam, celecoxib, parecoxib, rofecoxib, valdecoxib, and salts thereof. Examples of opioid analgesics drugs such as alfentanil, allylprodine, alphaprodine, anileridine, benzylmorphine, bezitramide, buprenorphine, butorphanol, clonitazene, codeine, cyclazocine, desmorphine, dextromoramide, dexozine, diampromide, dihydrocodeine, dihydromorphine, dimenoxadol, dimepheptanol, dimethylthiambutene, dioxaphenylbutyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, morphine sulfate, myrophine, nalbuphine, narceine, nicomorphine, norlevorphanol, normethadonel, nalorphine, normorphine, norpipanone, opium, oxycodone, oxymorphone, papaveretum, pentazocine, phenadoxone, phenmorphan, phenazocine, phenoperidine, piminodine, piritramide, proheptazine, promedol, properidine, propiram, propoxyphene, sufentanil, tramadol, tiline, salts thereof, mixtures of any of the foregoing, mixed mu-agonists/antagonists, mu-antagonist combinations. Examples of suitable antihistamines include both sedating and non-sedating antihistamines, e.g., fexofenadine HCl- or dl-chlorpheniramine maleate, diphenhydramine, loratadine, desloratadine, meclizine, pheniramine, cetirizine, and promethazine. Examples of antitussive expectorants include, e.g., such as guaifenesin, dihydrocodeine phosphate, codeine phosphate, noscapine hydrochloride, phenylpropanolamine hydrochloride, potassium guaiacolsulfonate, cloperastine fendizoate, dextromethorphan hydrobromide and cloperastine hydrochloride. Examples of bronchodilators include, e.g., dl-methylephedrine hydrochloride and dl-methylephedrine saccharinate. Examples of decongestants include, e.g., pseudoephedrine hydrochloride, phenylephrine bitartrate, and pseudoephedrine sulfate.

One suitable combination includes guaifenesin.

A modified release benzonatate composition as described herein may contain one or more excipients selected from one or more bulking agents, binders, and lubricants. For example, the bulking agent is selected from microcrystalline cellulose and lactose monohydrate. In another embodiment, the binder is copovidone. In still another embodiment, the lubricant is selected from silicone dioxide and magnesium stearate.

Typically, a benzonatate composition as provided herein may contain a filler or a mixture of fillers in the range of about 10% w/w to about 50% w/w, about 20% w/w to about 40% w/w, or about 30% w/w of the total tablet or capsule weight. Suitable fillers may include, e.g., mannitol, lactose, maltose, fructose, sucrose, xylitol, maltitol, microcrystalline cellulose, dicalcium phosphate, guargum, xantham gum, tragacanth gum, pre-gelatinized starch, compressible sugar, calcium carbonate, magnesium carbonate, calcium sulfate, dextrates, maltodextrin. In one embodiment, a benzonatate tablet contains a blend microcrystalline cellulose lactose monohydrate.

The binder for a composition as provided herein may be absent (i.e., 0%), or optionally, present in an amount of about 1% w/w to about 15% w/w of the total tablet weight. Examples of suitable binders include polyvinylpyrrolidone (povidone), hydroxypropyl methyl cellulose, hydroxypropyl cellulose, hydroxyethyl cellulose, methyl cellulose, polyvinyl alcohol, starch, acacia, alginic acid, sodium alginate.

Optionally, a colorant may be provided to the tablet to provide a desired visual appeal or trade dress. Such colorants may be added in the range of about 0.001% w/w to about 1% w/w, or about 0.01% w/w to about 0.08% w/w or about 0.05% w/w, based on the total weight of the tablet (exclusive of any non-functional coating). Such colorants are available from a variety of commercial sources including, e.g., Colorcon, Noveon, and Spectra.

In order to facilitate production of a benzonatate composition as provided herein, excipients such as lubricants and glidants may be utilized. A lubricant may be utilized in an amount of about 0.1% w/w to about 5% w/w, about 0.2% w/w to about 4.5% w/w, or about 1.5% w/w to about 3% w/w of the total weight of the tablet. Examples of lubricants may include, e.g., talc, magnesium searate, sodium stearyl fumarate, stearic acid, zinc stearate, calcium stearate, magnesium trisilicate, polyethylene glycol, and blends thereof. Examples of suitable glidants include, e.g., silicon dioxide and tribasic calcium phosphate. In one embodiment, the glidant is silicon dioxide which is used in an amount of about 0.001% w/w to about 0.1% w/w or about 0.05% w/w.

Optionally, other excipients may be selected from conventional pharmaceutically acceptable carriers or excipients and well established techniques. Without being limited thereto, such conventional carriers or excipients include diluents, binders and adhesives (i.e., cellulose derivatives and acrylic derivatives), lubricants (e.g., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

The solid benzonatate compositions described herein may contain one of the following combination of components in its core. The components listed with an * are optional excipients. * Components are optional. Values are given in the following tables.

| Component | Broad Range w/w | Narrower Range w/w |
| --- | --- | --- |
| Range of benzonatate to silicate in adsorbate | 50-70 wt % benzonatate based on total adsorbate weight | 55-65% wt % benzonatate based on total adsorbate weight |
| Benzonatate adsorbate | 20-40 wt % (based on total weight of adsorbate in total tablet prior to optional reverse enteric coating) | 25-35% (based on total weight of adsorbate in total tablet prior to optional reverse enteric coating) |
| Modified Release Matrix-forming Substance: (a) Hydrophobic Wax/Waxy Substance, (b) Hydrophilic Polymer, or Combinations | 5-40% (based on total weight in tablet prior to optional reverse enteric coating) | 5-20% |
| *Filler(s)/bulking agent(s) Microcrystalline cellulose | 10%-50% | 15%-40% |
| Lactose monohydrate | 5-20% (12%-16%) 5-35% | |
| *Binder(s) | 1%-15% | 3%-10% |

-continued

| Component | Broad Range w/w | Narrower Range w/w |
|---|---|---|
| *Lubricant(s) | 0.1%-2% | 0.6%-1% |
| Silicon dioxide | 0.5%-2% | 0.7%-1.5% |
| Magnesium stearate | 0.1%-1% | 0.3%-0.8% |
| *Colorant | 0.01%-0.5% | 0.02%-0.08% |

In another illustrative example, a benzonatate composition as provided herein has the following components:

| Component | Broad Range w/w | Narrower Range |
|---|---|---|
| B. Benzonatate - weak acidic ion exchange resin complex in matrix with modified release wax or hydrophilic polymer | 25%-100% | 30%-60% |
| C. Coated benzonatate - ion exchange resin complex -(optional) matrix (solvent-based ethylcellulose coating over matrix) | 25%-1020% | 30%-60% |
| *Filler(s)/bulking agent(s) | 10%-50% | 15%-40% |
| Microcrystalline cellulose | 5%-15% | |
| Lactose monohydrate | 5%-35% | |
| *Binder(s) | 1%-15% | 3%-10% |
| *Lubricant(s) | 0.1%-2% | 0.6%-1% |
| Silicon dioxide | 0.5%-1.6% | 0.7%-1% |
| Magnesium stearate | 0.1%-1% | 0.3%-0.8% |
| *Colorant | 0.01%-0.5% | 0.02%-0.08% |

In one embodiment, the tablet has a hardness of about 5 kilopond (kp) to about 25 kp, about 8 to about 20 kp, or 10 to about 16 kp. One (1) kilopond is one kilogram of force (kgf). Newtons (N) are the SI unit of force and the SI standard for tablet hardness testing. 1 kilopond (kp) is equal to 9.80665 Newtons (N). Presented in Newton rounded to the nearest five, the tablet has a hardness of about 45 N to about 245 N, about 75 N to about 200 N, or about 95 N to about 160 N. Optionally, the hardness may be dose proportional, with lower doses having lower hardness levels. For example, a 20 mg tablet may have a hardness in the range of about 10 to about 12 kp (about 98 N to about 118 N), a 30 mg tablet may have a hardness in the range of about 12 to about 14 kp (about 118 N to about 137 N), and a 40 mg tablet may have a hardness in the range of about 14 kp to about 16 kp (about 137 N to about 156 N). In one embodiment, the hardness is determined following compression and prior to application of any color or other non-functional tablet coating as defined herein. In one embodiment, the tablets meet the USP Friability requirement. In one embodiment, the friability of both the intact tablet and the tablet portions are less than about 1. See, e.g., USP35, General Information/(1216) Tablet Friability, p. 867-868, US Pharmacopiea (Dec. 1, 2012).

A functional coating such a reverse enteric coating may be applied to a tablet as described herein. The tablet may be loaded into a capsule alone, or manufactured as mini-tablets which are loaded into a capsule shell. Alternatively, the power may be loaded into a capsule which capsule shell is provided with the reverse enteric coating. In contrast to an enteric coating which is designed to avoid dissolution in the acidic pH of the stomach, a reverse enteric coating is designed to solubilize or swell in the presence of low acid environments (e.g., less than about pH 4, or less than about pH 3.5, or less than about pH 3). A reverse enteric coating is pH-dependent and designed not to solubilize or swell in pH greater than about pH 4, or greater than about 4.5. One suitable reverse enteric polymer is an acrylate polymer or copolymer. Particularly suitable reverse enteric coats include those polymers which can be applied as aqueous dispersions. One suitable aqueous dispersion is based on methyl methacrylate and diethylaminoethyl methacrylate copolymer. One example of such a reverse enteric coat is Kollicoat® Smartseal 30D, which is an aqueous polymeric dispersion with a solids concentration of approximately 30%. It contains methyl methacrylate and diethylaminoethyl methacrylate copolymer stabilized with approximately 0.6% macrogol cetostearyl ether and 0.8% sodium lauryl sulfate. Still other reverse enteric polymers include, e.g., Eudragit® E 100 (Evonik), Eudragit® EPO (Evonik), methyl methacrylate, hydroxyl ethyl methacrylate and a random terpolymer based on methyl methacrylate, 2-hydroxy ethyl methacrylate and 4-vinylpyridine. The EUDRAGIT® EPO is Poly(butyl methacrylate-co-(2-dimethylaminoethyl) methacrylate-co-methyl methacrylate) 1:2:1 (CAS number: 24938-16-7), i.e., a cationic copolymer based on dimethylaminoethyl methacrylate, butyl methacrylate and methyl methacrylate. The commercial Eudragit® EPO Ready Mix consists of basic butylated methacrylate copolymer, sodium lauryl sulphate, stearic acid and talc. However, other surfactants, including other anionic surfactants, may be substituted for sodium lauryl sulfate in other formulations. Examples of suitable surfactants other than the anionic surfactant sodium lauryl sulfate are known to the skilled artisan. Similarly, lubricants other than stearic acid and glidants other than talc are known in the art and may be selected. Still other reverse enteric polymers are described, and may be made, as described, e.g., US 2006/062844 (2006); US 2005/0136114, U.S. Pat. No. 7,294,347, the disclosure of which is incorporated herein by reference. Weight percentages of these coatings, when present, are provided as weight added, in an amount of about 5% to about 60%, or about 5% to about 20%, or about 8 to about 12% weight added to the finished tablet or capsule.

As used herein, a "non-functional coating" refers to a coating which contributes no detectable modified release functions. The non-functional coating may be a polymer may serve as a moisture barrier to preserve the integrity of the tablet during storage or to facilitate application of a color coating layer. Additionally or alternatively, the non-functional coating may provide a color coating layer or improve the "smoothness" or mouth feel of the tablet. In one embodiment, the non-functional coating may increase the hardness of the tablet. Weight percentages of these non-functional coatings, where present, are provided as weight added, in an amount of about 1% to about 20%, or about 2% to about 10%, or about 3% to about 5% weight added to the finished tablet.

In one embodiment, a 12-hour benzonatate composition as provided herein is characterized by having an in vitro dissolution, wherein no more than about 20% is released within 30 minutes, no more than about 25% is released within about 1 hour, no more than about 45% is release within 3 hours, no more than about 70% is released within 6 hours, and no more than about 95% is released within 12 hours. In another embodiment, about 15% is released within about 30 minutes, about 20% is released within 1 hour, about 41% is released within about 3 hours, about 64% is released within about 6 hours, and about 90% is released within about 12 hours. Percent release at the different times may be assessed using the following dissolution parameters: App (II) Paddle, 50 rpm, Media: 0.05 M Sodium Phosphate, pH 6.8 (900 mL), Temp 37° C., or another suitable assay. See, e.g., Example 5.

In another embodiment, rather than being compressed into a tablet, the benzonatate modified release powder can be loaded into a soft or hard shell capsule. Suitable soft shell capsules include standard two piece gelatin capsules which typically range from about 10 to about 88 mm when fitted together (locked). Hard shell capsules may be in the same size range. While capsules may have increased risk of disuse, such capsules facilitate the combination of an additional pharmaceutically active ingredient which is in immediate release form or in a modified form but which is not within the solid dispersion of the waxy matrix. One of skill in the art can readily prepare these capsules given the guidance provided herein, in view of that which is known to those of skill in the art.

Coated Benzonatate Tablets

Optionally, a benzonatate tablet or capsule as described herein comprises a benzonatate-weak cation exchange resin complex which is coated with a sufficient amount of a non-aqueous, solvent-based ethycellulose pH-independent, water-insoluble, water-permeable, barrier coating to provide the 12-hour release profile which avoids the release of any deleterious amount of benzonatate in the buccal cavity and which is characterized by less than about 35% of the benzonatate is released in 45 minutes in the USP standard in vitro dissolution media and less than about 60% of the benzonatate is released within about one hour, as determined using an in vitro dissolution paddle test described herein.

The benzonatate-weak cation exchange resin complex is prepared as described above. Optionally, following complexation, all or a portion of the resulting complex may be granulated with a suitable impregnating agent to reduce swelling prior to coating with a solvent-based ethylcellulose coating. This impregnating (solvating) agent is a hydrophilic (water soluble) agent exemplified by those materials described for example in U.S. Pat. No. 4,221,778 and published US Patent application Publication No. US 2003/009971 A1, the disclosures of which are incorporated herein by reference. Specific examples of suitable impregnating agents include propylene glycol, polyethylene glycol, polyvinyl alcohol, polyvinyl pyrrolidone (e.g., KOLLIDON™ K30) mannitol, methyl cellulose, hydroxypropyl methylcellulose, hydroxypropyl cellulose, and sorbitol. Typically, such impregnating agents are used at a weight ratio of about 5 wt % to about 30 wt % impregnating agent to benzonatate-weak cation exchange resin. Optionally, the resulting granules are passed through a 40 mesh screen to provide particles of no more than about 420 microns. These granules are then coated with a solvent-based ethylcellulose coating. In one embodiment, about 5% w/w to about 20% w/w of a suitable plasticizer is added to the ethylcellulose coating.

In one embodiment, the non-aqueous solvent-based ethylcellulose [such as in commercially available as the line of ETHOCEL™ products by Dow] is used. Dow's web site describes three of these products, Std 7 (viscosity of 6-8 mPa-s (CP); Std 10 (9-11 mPa-s (CP); Std 20 (18-22 mPa-S), each of which has a 48.0-49.5% ethoxyl content) as being useful for tablet coating. Further, optionally combining one of these polymers in combination with a water-soluble active and/or water-soluble excipient such as a METHOCEL™ cellulose ether and/or CARBOWAX™ polyethylene glycols is further described. Optionally, such a coating may be modified in order to achieve the preferred release profile characteristics defined herein, e.g., by addition of a sufficient amount of plasticizer to improve flexibility and/or by curing to a sufficient temperature to achieve the desired release rate.

A coating as described herein may be applied using techniques described by the polymer manufacturer and/or techniques which are known to those of skill in the art. Suitable methods and apparatus have been described in the patent and non-patent literature and include, e.g., spraying in a fluid bed processor. Spraying the coating solution in a fluid bed processor (e.g., VECTOR™ FLM-1 fluid bed processor) using Wurster process. The coated complex can then be dried. The dried, optionally cured, coated benzonatate-weak acid cation exchange resin complex-optional matrix may be passed through a suitable screen in order to ensure that the particle size is in the desired range, e.g., capable of passing through a standard 40 mesh screen. In one embodiment, the dried, optionally cured, coated ion exchange resin complex matrix granules have a mean particle size in the range of about 100 microns to about 450 microns, or about 150 to about 300 microns.

This ethylcellulose-coated benzonatate-ion exchange resin complex may be compressed into a tablet or filled into a capsule as described herein. Optionally, these compositions may be prepared using excipients and methods described above.

Method of Treating Cough and Cold Symptoms

In one aspect, the compositions described herein are useful in suppressing coughs for at least about 12 hours following administration of a single oral dose of a benzonatate modified release solid oral tablet or capsule composition as described herein. The compositions provides convenience for patients with cough symptoms, as presently available immediate release compositions are 8 hour products. Further, since the compositions provide the modified release benzonatate in tablet or powder form, these compositions reduce the risk of major oropharyngeal anesthesia side effects resulting from accidental chewing or crushing associated with the softgel forms of benzonatate.

In one embodiment, the patient receives a single 12-hour dose containing about 100 to about 200 mg benzonatate in a solid oral composition as provided herein. A 12-hour antitussive modified release solid oral tablet or capsule composition as described herein provides benzonatate in a matrix, optionally with a reverse enteric coat. The matrix is a homogenous solid dispersion comprising a benzonatate component in a matrix formed with a hydrophilic polymer forming a modified release matrix or hydrophobic wax or waxy-like substance. In one embodiment, the benzonatate component is an adsorbate comprising a benzonatate and one or more adsorbent (e.g., a nonmetallic based silica or silicate). In another embodiment, the benzonatate component is a benzonatate-weak acidic ion exchange resin complex. The matrix forming polymer may be at least one pharmaceutically acceptable modified release pH-independent, high melt temperature, matrix-forming water-insoluble wax or waxy substance in an amount effective to provide a 12-hour modified release profile to the benzonatate. Additionally, or alternatively, the matrix forming polymer is a pH, independent, hydrophilic polymer as defined previously in this specification. Suitably, there is substantially no benzonatate release from the composition in the buccal cavity or esophagus and no more than about 55%, no more than about 45%, no more than about 30%, or no more than about 25%, or no more than about 20% of the benzonatate is released within 1 hour following administration. Suitably, this release profile provides for most of the benzonatate to be released outside of the buccal cavity or esophagus with release beginning in the stomach.

The following examples are provided to more specifically illustrate the compositions of the present invention and not intended to be limiting. They are for illustrative purposes only and it is realized that changes and variations can be made without departing from the spirit and scope of the invention.

EXAMPLES

As used in the following examples, the term "intragranular" refers to granulations prepared with Benzonatate and the adsorbate and/or wax and/or hydrophilic polymer. "Extragranular" refers to excipients added externally to granulations.

Example 1

Benzonatate ER Tablet 150 mg Using Calcium Silicate as Adsorbent and Glyceryl Behenate as Modified Release Agent in Matrix

| Ingredient | % w/w | Qty/Tablet (mg) |
|---|---|---|
| Intra granular | | |
| Benzonatate | 23.1 | 150.0 |
| Glyceryl Behenate (Compritol 888 ATO) | 6.2 | 40.0 |
| Calcium Silicate (Zeopharm 600) | 11.1 | 72.0 |
| Extra granular | | |
| Lactose monohydrate (Flowlac 100) | 8.9 | 58.0 |
| Tri calcium phosphate (Tri-tab) | 33.8 | 220.0 |
| Copovidone (Kollidon VA64) | 3.1 | 20.0 |
| Glyceryl Behenate (Compritol 888 ATO) | 13.1 | 85.0 |
| Silicon dioxide (Syloid) | 0.8 | 5.0 |
| TOTAL | 100.0 | 650.0 |

Batch Size: ~60 tablets

To prepare the benzonatate-glyceryl behenate-calcium silicate adsorbate blend (intra-granular), the glyceryl behenate (6.2% w/w) was melted at 75° C. and the benzonatate (23.1% w/w) was slowly incorporated into it. After mixing the above molten Benzonatate-Glyceryl Behenate for 5 minutes, 11.1% w/w calcium silicate was added to it and mixed uniformly at room temperature. The mixture was passed through a 710 micron (#25 mesh) screen. This resulting intra-granular benzonatate-glycerol behenate adsorbate blend was combined with the extra-granular powder blend prepared as follows.

To prepare the extra-granular powder blend, lactose monohydrate (8.9% w/w), tricalcium phosphate (33.8% w/w), copovidone (3.1% w/w), glyceryl behenate (13.1% w/w) were passed through a 600 micron (#30 mesh) screen and mixed with the benzonatate-calcium silicate adsorbate-glycerol behenate blend for 10 minutes to form a final blend. The silicon dioxide was passed through a 600 micron (#30 mesh) screen and mixed with the blend for 2 minutes. The final blend comprising the benzonatate-calcium silicate adsorbate-glycerol behenate-matrix was compressed in a rotary press with Tooling: 0.2900×0.6320 inches capsule shaped (Hardness: 5 kP).

Example 2

Alternate Benzonatate ER Tablet 150 mg Using Calcium Silicate as Adsorbent and Glyceryl Behenate as Modified Release Agent in Matrix A. Benzonatate Adsorption with Calcium Silicate ("Benzonatate-Calcium Silicate Adsorbate")

| Ingredients | % w/w | Qty (g) |
|---|---|---|
| Benzonatate | 60.0 | 240.0 |
| Calcium Silicate (ZeoPharm ® 600) | 40.0 | 160.0 |
| Total | 100.0 | 400.00 |

Using the ingredients and amounts in the preceding table, calcium silicate was mixed at slow speed in a high shear granulator (Impeller: 250 rpm and Chopper: 3200 rpm). The liquid benzonatate was added to this mixture at slow speed (Impeller: 250 rpm and Chopper: 3200 rpm) at a rate of approximately 7 g/minute. The resulting benzonatate-calcium silicate adsorbate granules formed were passed through a 425 micron screen.

The amount of benzonatate in an adsorbate may be determined using a suitable assay. The assay used for the calculations described herein involve comparing the chromatographic peak areas relative to the reference standard obtained by injecting 15 μL sample into a HPLC system equipped with a $C_{18}$ column maintained at 40° C. and a UV detector set at 310 nm. The mobile phase consisted of mobile phase A (65% 0.015M O-Phosphoric:35% Acetonitrile v/v) and mobile B (30% 0.015M O-Phosphoric Acid: 70% Acetonitrile v/v) where a gradient program shown in the below table was run at a flow rate of 2 mL/min.

| Time, min | Mobile Phase A, % | Mobile Phase B, % |
|---|---|---|
| 0 | 100 | 0 |
| 8 | 100 | 0 |
| 20 | 35 | 65 |
| 21 | 100 | 0 |
| 30 | 100 | 0 |

B. Step 2: Tablet Preparation:

| | Ingredient | % w/w | Qty/Tablet (mg) |
|---|---|---|---|
| | Intragranular | | |
| 1 | Benzonatate-Calcium Silicate adsorbate (Assay 60.88%) - From Step A | 37.9 | 246.4 |
| 2 | Lactose Monohydrate, NF (Flow Lac 100) | 24.9 | 162.1 |
| 3 | Microcrystalline Cellulose (Ceolus 711) | 12.3 | 80.0 |
| 4 | Copovidone (Kollidon VA 64) | 10.8 | 70.0 |
| | Extragranular | | |
| 5 | Glyceryl Behenate (Compritol 888 ATO) | 13.1 | 85.0 |
| 6 | Silicon Dioxide (Syloid 244) | 1.0 | 6.5 |
| | TOTAL | 100.0 | 650.0 |

Batch Size: 120 tablets

The benzonatate-calcium silicate adsorbate from Part A of this example, lactose monohydrate, microcrystalline cellulose and copovidone were passed through 600 micron (#30 mesh) screen and mixed for 10 minutes. The blend was passed through the roller compactor with the following parameters: Roll Speed: 1 rpm, Screw Speed: 8 rpm, Roll Pressure: 1800 psi. The compacted sheets were passed through 850 micron (#20 mesh) screen. The granules were passed through roller compactor again using the above parameters. The compacted sheets were sieved through a 850 micron screen.

The glyceryl behenate was passed through a 850 micron screen and mixed with above prepared granules for 10 minutes to form a final blend comprising the benzonatate-calcium silicate adsorbate-glyceryl behenate matrix. The silicon dioxide was then passed through 600 micron screen and mixed with the above blend for 2 minutes. The blend was compressed with Tool: 0.2900"×0.6320" ("K 60" and Plain); Hardness: 8 Kp In vitro dissolution of the compressed tablet was assessed using the following assay parameters. The Dissolution parameters: App (II) Paddle, 50 rpm, 0.05M Sod. Phosphate, pH 6.8 (900 mL), Temp 37° C.):

| Time | 30 min | 1 hr | 3 hr | 6 hr | 12 hr |
|---|---|---|---|---|---|
| % Release | 16 | 20 | 41 | 64 | 91 |

Example 3

Benzonatate ER Tablet 150 mg Using Calcium Silicate as Adsorbent and Combination of Cetyl Alcohol & Stearyl Alcohol as Modified Release Agent in Matrix

| Ingredient | % w/w | Qty/Tablet (mg) |
|---|---|---|
| Intra granular | | |
| Benzonatate | 30.0 | 150.0 |
| Cetyl Alcohol (Alfol 16 NF) | 3.6 | 18.0 |
| Stearyl Alcohol (Alfol 18 NF) | 4.4 | 22.0 |
| Extra granular | | |
| Calcium Silicate (Zeopharm 600) | 14.0 | 70.0 |
| Microcrystalline Cellulose PH 102 (Avicel 102) | 5.0 | 25.0 |
| Lactose monohydrate NF (Flowlac 100) | 41.4 | 207.0 |
| Silicon dioxide (Syloid) | 1.0 | 5.0 |
| Magnesium Stearate (Hyqual) | 0.6 | 3.0 |
| TOTAL | 100.0 | 500.0 |

Cetyl alcohol (3.6% w/w) and Stearyl alcohol (4.4% w/w) were melted at 50° C. and benzonatate (30.0% w/w) was slowly incorporated into the melted waxy mixture. The calcium silicate, microcrystalline cellulose, and lactose monohydrate were granulated with the molten mixture. The resulting adsorbate-matrix was passed through a 710 micron screen. Following this step, silicon dioxide was passed through a 600 micron screen and mixed with the above adsorbate-matrix blend for 2 minutes in a beaker. The magnesium stearate was passed through a 600 micron screen and mixed with adsorbate-matrix-silicon dioxide blend for 2 minutes. The final blend was then compressed in a rotary press with Tooling: 0.2730×0.5950 inches capsule shaped (Hardness: 5 kp)

Example 4

Benzonatate ER Tablet 150 mg Using Amberlite IRP64 Resin as Adsorbent and Glyceryl Behenate as Modified Release Agent in Matrix (Direct Compression)

A. Benzonatate-Ion Exchange Resin Complex (Benzonatate Resin)

| Ingredients | % w/w | Qty (g) |
|---|---|---|
| Purified water | 40.0 | 266.7 |
| Benzonatate | 30.0 | 200 |
| Amberlite ™ IRP64 | 30.0 | 200 |

The Benzonatate and water were mixed to dissolve the liquid benzonatate. The resulting solution was sprayed onto Amberlite™ IRP64 resin with continuous mixing in the Key High™ shear granulator to form a uniform mass (impellor speed: 250 rpm; chopper speed: 3200 rpm; spray rate: 30 g/min). Benzonatate-ion exchange resin complex granules formed were dried in an oven at 40° C. overnight. The benzonatate-ion exchange resin complex granules finally were passed through a 425 micron screen.

B. Formulation for Benzonatate ER Tablet 150 mg Using Benzonatate-Ion Exchange Resin and Glyceryl Behenate

| Ingredient | % w/w | Qty/Tablet (mg) |
|---|---|---|
| Benzonatate - Ion Exchange Resin Complex from Part A | 33.5 | 301.8 |
| Lactose Monohydrate (Flowlac 100) | 30.1 | 271.2 |
| Microcrystalline Cellulose 102 (Avicel PH 102) | 11.4 | 103.0 |
| Glyceryl Behenate (Compritol 888 ATO) | 13.9 | 125.0 |
| Copovidone (Kollidon VA64) | 10.0 | 90.0 |
| Silicon Dioxide (Syloid) | 1.0 | 9.0 |
| TOTAL | 100.0 | 900.0 |

Batch Size: 60 tablets

The benzonatate-ion exchange resin complex from Part A, lactose monohydrate, microcrystalline cellulose, glyceryl behenate and copovidone were passed through a 710 micron screen and mixed for 10 minutes. The silicon dioxide was passed through a 600 micron screen and mixed with the above blend for another 2 minutes to provide the benzonatate-ion exchange resin complex-matrix. The final blend was compressed on a rotary tablet press with 0.3310×0.7210 in caplet tool (Hardness: 6-7 kP).

Example 5

Benzonatate ER Tablet 150 mg Using Magnesium Aluminosilicate as Adsorbent and Glyceryl Behenate as Modified Release Agent in Matrix (Direct Compression)

A. Benzonatate-Magnesium Aluminosilicate Adsorbate

| Ingredients | % w/w | Qty (g) |
|---|---|---|
| Purified water | 40.0 | 160.0 |
| Benzonatate | 30.0 | 240.0 |
| Magnesium Aluminometasilicate (Neusilin ® UFL2) | 30.0 | 160.0 |
| Total | 100.0 | 460.0 |

Liquid Benzonatate and purified water were mixed to dissolve the benzonatate. The benzonatate solution was sprayed on to Magnesium Aluminometasilicate with continuous mixing in the Key High™ shear granulator using the same impeller and chopper speeds as in Example 4 to form a uniform mass. The benzonatate silicate adsorbate granules were dried in fluid bed equipment to moisture content between 1-3%. The adsorbate granules were passed through a 425 micron screen. The retained adsorbate granules were passed through the Fitz Mill 3200 rpm knife using mesh screens 0033 (840 microns) and 0020 (510 microns). The adsorbate granules were finally passed through a 425 micron screen again.

B. Benzonatate ER Tablet 150 mg Using Benzonatate Magnesium AlumuinoSilicate Adsorbate and Glyceryl Behenate

| Ingredient | % w/w | Qty/Tablet (mg) |
|---|---|---|
| Benzonatate Magnesium Aluminosilicate Adsorbate of Part A | 28.7 | 244.3 |
| Lactose monohydrate (Supertab 11SD) | 32.8 | 278.7 |
| Microcrystalline Cellulose 102 (Avicel PH 102) | 12.1 | 103.0 |

-continued

| Ingredient | % w/w | Qty/Tablet (mg) |
|---|---|---|
| Glyceryl Behenate (Compritol 888 ATO) | 14.7 | 125.0 |
| Copovidone (Kollidon VA64) | 10.6 | 90.0 |
| Silicon Dioxide (Syloid) | 1.1 | 9.0 |
| TOTAL | 100.0 | 850.0 |

Batch Size: 60 tablets

All of the ingredients except silicon dioxide were first passed through a 710 micron screen and mixed for 10 minutes. The silicon dioxide was passed through a 600 micron screen and mixed with the above blend for another 2 minutes. The final benzonatate-magnesium aluminosilicate adsorbate-matrix was compressed on a rotary tablet press with 0.3600× 0.7480 inch oval tool (Hardness: 6-7 kP).

The in vitro dissolution of this tablet was assessed using the following dissolution parameters: App (II) Paddle, 50 rpm, Media: 0.05 M Sodium Phosphate, pH 6.8 (900 mL), Temp 37° C.

| Time (hrs) | 30 min | 1 | 3 | 6 | 12 |
|---|---|---|---|---|---|
| % Release | 16 | 23 | 41 | 63 | 91 |

Example 6

Benzonatate ER Tablets 150 mg Using Benzonatate-Weak Acidic Cation Exchange Resin Complex Coated with Non-Aqueous Ethylcellulose Barrier Coating A. Complexation of Benzonatate (Benzonatate Resin)

| Ingredients | % w/w | Qty (g) |
|---|---|---|
| Purified water | 40.0 | 266.7 |
| Benzonatate | 30.0 | 200 |
| Amberlite IRP64 | 30.0 | 200 |

Purified Water was weighed and Benzonatate was admixed in it. This solution was sprayed onto the Amberlite IRP64 weak acidic cation exchange resin with continuous mixing in the Key High shear granulator (impellor speed 250 rpm, chopper speed 3200 rpm, spray rate 30 g/min) to form a uniform mass. The granules formed were dried in an oven at 40° C. overnight. Finally, the granules were passed through a 425 micron screen.

B. Granulation of Benzonatate-Weak Acid Cationic Exchange Resin Complex (Benzonatate-Ion Exchange Resin Complex-Matrix)

| Ingredients | % w/w | Qty (g) |
|---|---|---|
| Hypromellose (Methocel E5) | 1.7 | 12.5 |
| Ethanol 190 Proof | 31.7 | 237.5 |
| Benzonatate - Cation Exchange Resin of Part A | 66.7 | 500 |
| Total | 100.0 | 750.0 |

Hypromellose was slowly added to Ethanol and mixed till completely dissolved to give 'Hypromellose solution'. The benzonatate-cation exchange resin complex prepared in step (A)1 was mixed at slow speed in the Key High shear granulator (Impellor 250 rpm, Chopper 3200 rpm). The Hypromellose solution prepared above was sprayed at slow speed on to the Benzonatate resin (Impellor 250 rpm, Chopper 3200 rpm). The granulated benzonatate-cation exchange resin complex-matrix was passed through a 500 micron screen. Drying was not required as the moisture content was only 9.49%.

C. Coating Benzonatate-Ion Exchange Resin Complex-Matrix with Ethyl Cellulose at 20% Level (Benzonatate ME20 Resin)

| Coating solution Ingredients | % w/v | Qty (g) |
|---|---|---|
| Triacetin | 1.0 | 11.0 |
| Ethanol 190 proof | 89.0 | 979.0 |
| Ethyl cellulose (Ethocel 10 Premium) | 10.0 | 110.0 |
| Total | 100.0 | 1100.0 |

Ethocel 20% Coating:

| Ingredients | Qty (g) |
|---|---|
| Benzonatate - ion exchange resin complex - matrix of Part B | 450 |
| Coating Solution | 818 |

To prepare the coating solution, triacetin was dissolved in ethanol. Ethyl cellulose was added slowly and mixed until it was completely dissolved. The coating solution prepared was sprayed onto benzonatate-cation exchange resin complex-matrix prepared according to Part B in the fluid bed equipment such that 20% solid content was loaded onto the benzonatate-cation exchange resin complex-matrix. The coated benzonatate-cation exchange resin complex-matrix temperature was maintained at approximately 35° C. in the fluid bed equipment.

D. Formation of Benzonatate ER Tablet 150 mg

| Ingredient | % w/w | Qty/Tablet (mg) |
|---|---|---|
| Coated Benzonatate - cation exchange resin complex - matrix of Part C | 27.0 | 243.4 |
| Benzonatate - cation exchange resin complex of Part A | 11.2 | 100.6 |
| Lactose Monohydrate (Supertab ® 11SD) | 27.6 | 248.5 |
| Microcrystalline Cellulose 102 (Avicel ® 102) | 31.1 | 280.0 |
| Povidone K90F (Kollidon 90) | 1.7 | 15.0 |
| Silicon Dioxide (Syloid ®) | 0.6 | 5.0 |
| Magnesium Stearate (Hyqual ®) | 0.8 | 7.5 |
| TOTAL | 100.0 | 900.0 |

Batch Size: 100 Tablets

Coated benzonatate-cation exchange resin complex-matrix of Part C, benzonatate-cation exchange resin complex of Part A, lactose monohydrate, microcrystalline cellulose and polyvinylpyrrolidone K90F were passed through a 710 micron screen and mixed for 10 minutes. Silicon dioxide was passed through a 600 micron screen and mixed with the above blend for 2 minutes. Magnesium stearate was passed through a 600 micron screen and mixed with the above blend for another 2 minutes. The final blend was compressed on rotary tablet press with 0.3310×0.7210 inches caplet tool (Hardness: 8-10 kP)

The in vitro dissolution profile of the tablet was assessed using the following dissolution parameters App (II), Paddle, 50 rpm, in a dissolution media of 0.05M Sodium Phosphate, pH 6.8 (900 mL), at a temperature of 37° C.

| Time (hrs) | 0.5 | 1 | 2 | 3 | 4 | 6 | 8 | 12 |
|---|---|---|---|---|---|---|---|---|
| % Release | 47 | 56 | 67 | 73 | 76 | 78 | 78 | 74 |

For comparative purposes, in vitro dissolution was also assessed in USP Media Water 900 mL App II, Paddle, 50 rpm.

| Minutes | 10 | 20 | 30 | 45 |
|---|---|---|---|---|
| % Release | 23 | 29 | 31 | 34 |

Example 7

Benzonatate ER Tablet 150 mg Using Calcium Silicate as Adsorbent and Glyceryl Behenate as Modified Release Agent in Matrix and Reverse Enteric Coating Step 1: Benzonatate Adsorption with Calcium Silicate ("Benzonatate-Calcium Silicate Adsorbate")

| No. | Ingredients | % w/w | Qty (g) |
|---|---|---|---|
| 1 | Benzonatate | 60.0 | 300.0 |
| 2 | Calcium Silicate (ZeoPharm ® 600) | 40.0 | 200.0 |
|  | Total | 100.0 | 400.00 |

Using the amounts shown in the preceding table, calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approx. 7 g/minute. The granules formed were passed through a 425 micron screen.

Step 2: Formulation Process:

The following table provides the components for a batch size of 1500 tablets.

|   | Ingredient | % w/w | Qty/Tablet (mg) | Qty (g) |
|---|---|---|---|---|
|   | Intragranular |   |   |   |
| 1 | Benzonatate-Calcium Silicate Adsorbate (Assay 60.66%) - From Step 1 | 29.1 | 247.3 | 370.92 |
| 2 | Lactose Monohydrate, NF (Flow Lac 100) | 29.1 | 247.7 | 371.58 |
| 3 | Microcrystalline Cellulose (Ceolus 711) | 16.7 | 142.0 | 213.00 |
| 4 | Copovidone (Kollidon VA 64) | 10.0 | 85.0 | 127.50 |
|   | Extragranular |   |   |   |
| 5 | Glyceryl Behenate (Compritol 888 ATO) | 13.1 | 111.0 | 166.50 |
| 6 | Silicon Dioxide (Syloid 244) | 1.0 | 8.5 | 12.75 |
| 7 | Magnesium Stearate | 1.0 | 8.5 | 12.75 |
|   | TOTAL | 100.0 | 850.0 | 1275.00 |

Using the amounts shown in the preceding table, the benzonatate-calcium silicate adsorbate prepared in step 1, lactose monohydrate, microcrystalline cellulose, and copovidone were passed through a 600 micron screen and mixed for 10 minutes. The resulting blend was passed through the roller compactor with the following parameters: Roll Speed: 1 rpm; Screw Speed: 8-12 rpm, Roll Pressure: 1800 psi. The compacted sheets were passed through a 850 micron screen.

In a separate process, glyceryl behenate was passed through 600 micron screen and mixed with above prepared granules for 10 minutes. Silicon dioxide was passed through 600 micron screen and mixed with the above blend for 2 minutes. Magnesium stearate was passed through 600 micron screen and mixed with the above blend for 2 minutes. The blend was compressed with Tool: 0.3600"×0.7480" (Oval tool, Plain); Hardness: 4-5 Kp.

Step 3: Coating with Kollicoat® Smartseal 30D

| Sr # | Ingredient | % w/w | Qty (g) |
|---|---|---|---|
| 1 | Kollicoat ® Smartseal 30D* aqueous polymeric dispersion | 33.3 | 166.65 |
| 2 | Tributyl citrate (TBC) | 1.5 | 7.50 |
| 3 | Butylated hydroxy- toluene | 0.1 | 0.50 |
| 4 | Talc | 8.0 | 40.00 |
| 5 | Purified Water | 57.1 | 285.35 |
|   | TOTAL | 100.0 | 500.00 |

*Kollicoat ® Smartseal 30D is an aqueous polymeric dispersion with a solids concentration of approximately 30%. It contains methyl methacrylate and diethylaminoethyl methacrylate copolymer stabilized with approximately 0.6% macrogol cetostearyl ether and 0.8% sodium lauryl sulfate.

Using the amounts shown in the table above, the coating was prepared as follows to provide a coating with a total solid content of 19.6% and a total polymer content of 10%. The final product contains a coating layer containing total polymer on dried film of about ~50% w/w polymer.

To prepare the coating, butylated hydroxy-toluene was dissolved in tributyl citrate with an arrow mixer for 20 minutes to form a Plasticizer Suspension. Separately, talc was homogenized in water using high shear mixer for 10 mins at 3200 rpm. The homogenized talc and the Plasticizer Suspension were slowly poured into the Kollicoat dispersion while stirring gently with an arrow mixer. This coating suspension was mixed for 2 hours, following which the coating suspension was passed through 180 micron screen and stirred continuously using a magnetic stirrer. The tablets were spray coated with this coating suspension in a fluid bed apparatus according to the following parameters and sampled out at 5% and 10% total polymer weight gain.

Process Parameters:

Inlet Temperature: 48° C.-55° C.

Exhaust Temp: 38° C.-40° C.

Air flow: 69 cfm

Spray rate: 1-2 g/min

The coated tablets were cured at 50° C. for 2 hours in hot air oven.

The in vitro dissolution profile of the resulting coated tablet was assessed using the following dissolution parameters App (II) Paddle, 50 rpm, in a dissolution media of 500 mL 0.1N HCl for 1 hr+400 mL phosphate buffer to a pH of 6.8, at a temperature of 37° C. The release percentages provided below are an average of four dissolution texts.

| Time | % Release |
|---|---|
| 0.5 hr | 16 |
| 1 hr | 27 |
| 2 hr | 44 |
| 3 hr | 61 |
| 4 hr | 83 |
| 6 hr | 97 |
| 8 hr | 99 |
| 12 hr | 100 |

Example 8

An Open-Label, Randomized, Two-Period Cross-Over, Single-Day Pilot Study to Compare the Relative Bioavailability of Benzonatate ER Tablets with an Equivalent Dose of a Reference Product (Tessalon®) Under Fasted Conditions in Healthy Adult Subjects The pharmacokinetics of benzonatate are not well characterized. The drug begins to act within 15-20 minutes after the administration of an immediate release formulation and the effect lasts for 3 to 8 hours. This study will assess the relative bioavailability of two benzonatate 150 mg extended-release tablets prepared as described in Example 7, which are administered twice daily (b.i.d) versus two Tessalon® 100 mg perles administered three times daily (t.i.d.) in healthy adult subjects. The pharmacokinetic results are provided in the Table below and illustrated in FIGS. 1A and 1B.

times were in the PK analysis. The following PK parameters will be estimated for benzonatate using a noncompartmental approach in SAS®: AUCinf: The area under the analyte concentration versus time curve from time zero to infinity. Cmax: Maximum measured analyte concentration over the sampling period. Tmax: Time of the maximum measured analyte concentration over the sampling period.

Analysis of variance (ANOVA) will be performed on log-transformed AUCinf and Cmax and on untransformed Tmax parameters. Using the same statistical model, the least-squares-means, the differences between the treatments least-squares-means and the corresponding standard errors of these differences will be estimated for log-transformed AUCinf and Cmax parameters. Based on these statistics, the ratios of the geometric means for treatments and the corresponding 90% confidence intervals and power will be calculated. These statistics will be used to evaluate the performance of the test formulation in relation to the reference product.

Benzonatate concentrations were measured from plasma by a validated LC/MS/MS analytical method. The following pharmacokinetic parameters were estimated using a noncompartmental approach: AUCinf, Cmax, and Tmax. Statistical Analysis: ANOVA (PROC GLM) will be performed on log-transformed AUCinf and Cmax and untransformed Tmax. Based on log-transformed data, ratios of the geometric means for treatments and the corresponding 90% confidence intervals will be calculated for AUCt, AUCinf and Cmax. These statistics will be used to evaluate the performance of the test formulation in relation to the reference product.

Summary of Study Results Based on Plasma Benzonatate Levels
Based on Raw Data

| Parameter | Trt | n | Arithmetic Mean (CV %) | Geometric Mean | Contrast | Ratio (%) | 90% Confidence Interval | Intra-Sbj CV(%) |
|---|---|---|---|---|---|---|---|---|
| Cmax (ng/mL) | A | 14 | 32.543 (43) | 30.115 | A vs B | 57.71 | 47.43-70.21 | 30 |
|  | B | 14 | 60.243 (54) | 52.188 |  |  |  |  |
| AUCinf (ng · h/mL) | A | 11 | 183.051 (62) | 150.268 | A vs B | 109.49 | 90.64-132.25 | 20 |
|  | B | 12 | 160.425 (50) | 137.244 |  |  |  |  |
|  |  | n | Median | Range |  |  |  |  |
| Tmax (h) | A | 14 | 12.00 | 1.00-16.00 |  |  |  |  |
|  | B | 14 | 9.00 | 0.50-17.00 |  |  |  |  |

Treatments:

Treatment A: The test benzonatate ER tablets were prepared as described in Example 7. A 300 mg dose of the test product (2 tablets) was administered with 240 mL and potable water in 2 equal doses (300 mg each), at 0 and 12 hours under fasting conditions.

Treatment B: A 200 mg dose of the reference product (2 perles) was administered in 3 equal doses (200 mg each), at 0, 8 and 16 hours under fasting conditions.

Dose: Test Product: 2×150 mg b.i.d. (total 600 mg dose)
Reference Product: 2×100 mg t.i.d. (total 600 mg dose)
Drug Administration: Test Product: two 150 mg tablets administered at 0 and
12 hours with 240 mL (±~5 mL) of potable water
Reference Product: two 100 mg perles administered at 0, 8 and 16 hours with 240 mL (±~5 mL) of potable water
14 subjects were in each group.

PK analysis was performed on available data from subjects in the PK dataset. The actual post-dose sample collection Example 9

Benzonatate ER Tablet 150 mg Using Calcium Silicate as Adsorbent and Reverse Enteric Coating (Cationic Copolymer Based on Dimethylaminoethyl Methacrylate, Butyl Methacrylate and Methyl Methacrylate)

1. Preparation of Benzonatate-Calcium Silicate Adsorbate

| Ingredients | % w/w | Qty (g) |
|---|---|---|
| Calcium Silicate (ZeoPharm ® 600) | 40.0 | 200.0 |
| Benzonatate | 60.0 | 300.0 |
| Total | 100.0 | 400.00 |

Using the amounts in the preceding table, the calcium silicate was mixed at slow speed in a high shear granulator (Impeller: 250 rpm; Chopper: 3200 rpm). Benzonatate was added to it at slow speed (Impeller: 250 rpm; Chopper: 3200 rpm) at a rate of approximately 7 g/minute. The benzonatate-calcium silicate adsorbate granules formed were passed through a 425 micron screen. Using the assay described in previous examples showed 60.66 wt % benzonatate based on the total weight of the benzonatate-calcium silicate adsorbate.

2. Preparation of Benzonatate ER Tablet

| No. | Ingredient | % w/w | Qty/Tablet (mg) | Qty/Lot (g) |
|---|---|---|---|---|
| | Intragranular | | | |
| 1 | Benzonatate-Calcium Silicate adsorbate of Part 1 (Assay 60.66%) | 27.5 | 247.7 | 99.08 |
| 2 | Lactose Monohydrate, NF (Flow Lac 100) | 15.3 | 138.0 | 55.20 |
| 3 | Microcrystalline Cellulose (Ceolus 711) | 16.4 | 148.0 | 59.20 |
| 4 | Glyceryl Behenate (Compritol 888 ATO) | 6.0 | 54.0 | 21.60 |
| | Extragranular | | | |
| 5 | Calcium Silicate (ZeoPharm ™ 600) | 6.8 | 60.8 | 24.32 |
| 6 | Microcrystalline Cellulose (Ceolus ™ 711) | 8.9 | 80.0 | 32.00 |
| 7 | Lactose Monohydrate, NF (Flow Lac ™ 100) | 6.4 | 57.5 | 23.00 |
| 8 | Copovidone (Kollidon ™ VA 64) | 10.0 | 90.0 | 36.00 |
| 9 | Colloidal Silicon dioxide (Aerosil ™ 200) | 1.1 | 9.5 | 3.80 |
| 10 | Magnesium Stearate (Hyqual Veg. Source) | 1.6 | 14.5 | 5.80 |
| | Total | 100.0 | 900.0 | 360.00 |

Batch Size: 400 tablets

Items 1, 2, 3 & 4 were mixed in KG5 [Key International] high shear granulator for 10 minutes (Impeller: 250 rpm; Chopper: 3200 rpm). Jacketed heat was turned on and the blend was mixed till the temperature reached 80° C. The blend was further mixed for 10 minutes at 80° C. The blend was spread out in stainless steel trays and cooled for 2 hours, following which the blend was passed through a 710 micron screen.

Items 5, 6, 7 & 8 were separately passed through a 710 micron screen and mixed with above blend (of items 1, 2, 3 and 4) for 10 minutes in a cube blender. Item 10 was passed through a 600 micron screen and 50% of it was mixed with the above blend for 3 minutes. The blend was passed through a TF mini [Vector Corporation] roller compactor (roll speed 1 rpm; pressure: 600 psi; screw speed 12 rpm). The ribbons were milled through Fitz Mill (FitzSpeed: 1200 rpm; Knife: forward; Screen 1650 micron (0065 screen) (The Fitzpatrick Company)). Item 9 was passed through a 600 micron screen and mixed with the above blend for 5 minutes. The remaining 50% of Item 10 was added to above blend and mixed for 3 minutes. The blend was compressed with Tool: 0.3310"× 0.7210" (Plain); Hardness: 10-12 Kp 3. Coating with "Eudragit® EPO Ready Mix" (Reverse Enteric Coat)

| Ingredient | % w/w | Qty/Lot (g) |
|---|---|---|
| Eudragit ® EPO Ready Mix* | 15.0 | 45.00 |
| Purified Water | 85.0 | 255.00 |
| Total | 100.0 | 300.00 |

The EUDRAGIT® EPO is a cationic copolymer based on dimethylaminoethyl methacrylate, butyl methacrylate and methyl methacrylate. Eudragit® EPO Ready Mix consists of basic Butylated methacrylate copolymer, sodium lauryl sulphate, stearic acid and talc. The mix reverse enteric coating mix was mixed with the purified water using a high shear mixer for 30 minutes at 2300 rpm to a total solid content of 15%.

The suspension was passed through a 500 micron screen and stirred continuously using a magnetic stirrer. Tablets prepared were coated with following parameters and sampled out at 10% solid content level. The coated tablets were pan dried at 40° C. for 30 minutes.

The process parameters were: Inlet Temperature: 35° C.; Exhaust Temp: 28° C.-30° C.; Air flow: 65 cfm; Spray rate: 1.5 g/min.

4. Coating with "Opadry® YS-1-19025-A" (Seal Coat)

| No. | Ingredient | % w/w | Qty/Lot (g) |
|---|---|---|---|
| 1 | Opadry ® YS-1-19025-A clear | 7.5 | 22.50 |
| 2 | Purified Water | 92.5 | 277.50 |
| | Total | 100.0 | 300.00 |

A clear seal coat Opadry® YS-1-19025-A solution was prepared by adding Item 1 to Item 2 (total solid content 7.5% w/v) and mixed for 60 minutes using an arrow mixer. Coating was performed on the reverse enteric coated tablets with following parameters and sampled out at 3% solid content level. Process parameters were: Inlet Temperature: 60° C.-65° C.; Exhaust Temp: 38° C.-48° C.; Air flow: 63 cfm; Spray rate: 1.5 g/min.

Example 10

Benzonatate ER Tablet 150 mg Using Calcium Silicate as Adsorbent and Hypromellose as Extended Release Agent in Matrix This formulation was prepared using hypromellose (also termed hydroxypropylmethylcellulose or HPMC) with a viscosity of 2663-4970 mPa-S, 19-24% methoxy, 7-12% hydroxypropyl, substitution 2208, and a bulk density of 0.12-0.15 g/cm$^3$ and a moisture content of 5% max.

1. Benzonatate with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm ® 600) | 38.5 | 200.0 |
| Total | 100.0 | 520.0 |

Using the amounts shown in the preceding table, calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approx. 7 g/minute. The benzonatate-calcium silicate adsorbate granules formed were passed through a 425 micron screen. Using the assay described herein, the amount of benzonatate was determined to be 60.66 wt % benzonatate based on the total weight of the adsorbate.

2. Benzonatate ER Tablet

| No. | Ingredient | % w/w | Qty/Tablet (mg) | Qty/Lot (g) |
|---|---|---|---|---|
| 1 | BEN-Calcium Silicate Adsorbate of Part 1 (Assay 60.66%) | 29.5 | 247.7 | 37.16 |
| 2 | Hypromellose K4M (Methocel ® K4M) | 32.1 | 270.0 | 40.50 |
| 3 | Microcrystalline Cellulose (Ceolus ® 711) | 16.2 | 135.8 | 20.37 |
| 4 | Lactose Monohydrate, NF (Flow Lac ® 100) | 8.8 | 74.0 | 11.10 |
| 5 | Copovidone (Kollidon ® VA 64) | 10.7 | 90.0 | 13.50 |
| 6 | Colloidal Silicon dioxide (Aerosil ® 200) | 1.1 | 9.0 | 1.35 |
| 7 | Magnesium Stearate (Hyqual ®) | 1.6 | 13.5 | 2.03 |
|  | Total | 100.0 | 840.0 | 126.00 |

Batch Size: 150 tablets

Items 1, 2, 3, 4 and 5 from the immediately preceding table were passed through a 710 micron and mixed in a cube blender for 10 minutes. Item 7 was passed through 600 micron screen and 50% of it mixed with the above blend (Items 1, 2, 3, 4, 5) for 2 minutes. The resulting blend with items 1-5 and 50% of item 7 was passed through a TFC mini roller compactor (roll speed 1 rpm; pressure: 1200 psi; screw speed 12 rpm; Vector Corporation). The ribbons were passed through 710 micron screen. Item 6 was passed through 600 micron screen and mixed with the above blend for 2 minutes. The remaining 50% of Item 7 was added to above blend and mixed for 2 minutes. The final blend was compressed with Tool: 0.3310"×0.7210" (Plain); Hardness: 5 Kp.

3. In-Vitro Dissolution (500 mL of 0.1N HCl for 1 hr+400 mL of Phosphate Buffer):

In order to assess the dissolution pattern of the tablet core prior to coating with a reverse enteric coating or an optional seal coat, in vitro dissolution profile of the tablet prepared according to Part 2 was assessed using the following dissolution parameters App (II) Paddle, 50 rpm, in a dissolution media of 500 mL 0.1N HCl for 1 hr+400 mL phosphate buffer to a pH of 6.8, at a temperature of 37° C. The release percentages provided below are an average of four dissolution vessels.

| Time (h) | 0.5 | 1 | 3 | 6 | 12 |
|---|---|---|---|---|---|
| % Released | 6 | 9 | 12 | 14 | 22 |

This tablet core may be coated with a reverse enteric coating and an optional seal coat.

Example 11

Benzonatate ER Tablet 150 mg Using Calcium Silicate as Adsorbent and Blend of Hypromelloses as Extended Release Agent in Matrix This formulation was prepared using a blend of two hypromelloses: (1) hyrpomellose with a viscosity of 2663-4970 mPa-S, 19-24% methoxy, 7-12% hydroxypropyl, substitution 2208, and a bulk density of 0.12-0.15 g/cm$^3$ and a moisture content of 5% max; and (2) hydromellose with a viscosity of 80-120 mPa-S, 19-24% methoxy, 7-12% hydroxypropyl, substitution 2208, and a moisture content of 5% max.

1. Benzonatate Adsorption with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm ® 600) | 38.5 | 200.0 |
| Total | 100.0 | 520.0 |

Using the ingredients in the immediately preceding table, calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approximately 7 g/minute. The benzonatate-calcium silicate adsorbate granules formed were passed through 425 micron screen. Using the assay described herein, the amount of benzonatate was determined to be 60.66 wt % benzonatate based on the total weight of the adsorbate.

2. Benzonatate ER Tablet

| No. | Ingredient | % w/w | Qty/Tablet (mg) | Qty/Lot (g) |
|---|---|---|---|---|
| | Intragranular | | | |
| 1 | BEN-Calcium Silicate Adsorbate of Part 1 (Assay 60.66%) | 27.5 | 247.7 | 37.16 |
| 2 | Hypromellose K100LV (Methocel ® K100LV) | 8.0 | 72.0 | 10.80 |
| 3 | Hypromellose K4M (Methocel ® K4M) | 12.0 | 108.0 | 16.20 |
| 4 | Calcium Silicate (Zeopharm ® 600) | 7.0 | 63.0 | 9.45 |
| 5 | Microcrystalline Cellulose (Ceolus ® 711) | 18.5 | 166.3 | 24.95 |
| 6 | Lactose Monohydrate, NF (Flow Lac ® 100) | 15.0 | 135.0 | 20.25 |
| 7 | Copovidone (Kollidon ® VA 64) | 10.0 | 90.0 | 13.50 |
| 8 | Magnesium Stearate (Hyqual ®) | 0.5 | 4.5 | 0.68 |
| | Extragranular | | | |
| 9 | Colloidal Silicon dioxide (Aerosil ® 200) | 1.0 | 9.0 | 1.35 |
| 10 | Magnesium Stearate (Hyqual ®) | 0.5 | 4.5 | 0.68 |
| | Total | 100.0 | 900.0 | 135.00 |

Batch Size: 150 tablets

Using the ingredients from the immediately preceding table, Items 1, 2, 3, 4, 5, 6 and 7 were passed through 850 micron screen and mixed in a cube blender for 10 minutes. Item 8 was passed through 600 micron screen and above blend for 2 minutes. The blend was passed through a roller compactor (roll speed 1 rpm; pressure: 1600 psi; screw speed 12 rpm). The ribbons were passed through Fitz mill (Knife forward, Speed: 1100 rpm, Screen 0065; Fitzpatrick Company). Item 9 was passed through 600 micron screen and mixed with the above blend for 3 minutes. Item 10 (600 micron screen) was added to above blend and mixed for 2 minutes. The blend was compressed with Tool: 0.3310"× 0.7210" (Plain); Hardness: 6 Kp.

3. In-Vitro Dissolution (500 mL of 0.1N HCl for 1 hr+400 mL of Phosphate Buffer):

In order to assess the dissolution pattern of the tablet core prior to coating with a reverse enteric coating or an optional seal coat, in vitro dissolution profile of the tablet prepared according to Part 2 was assessed using the following dissolution parameters App (II) Paddle, 50 rpm, in a dissolution media of 500 mL 0.1N HCl for 1 hr+400 mL phosphate buffer to a pH of 6.8, at a temperature of 37° C. The release percentages provided below are an average of four dissolution vessels.

| Time (h)   | 0.5 | 1 | 3  | 6  | 12 |
|------------|-----|---|----|----|----|
| % Released | 5   | 8 | 10 | 14 | 83 |

This tablet core may be coated with a reverse enteric coating and an optional seal coat.

Example 12

Benzonatate ER 150 Tablet with Benzonatate-Calcium Silicate Adsorbate and Using Controlled Release (CR) Hypromellose K100LV This formulation was prepared using the hypromellose with a viscosity of 80-120 mPa-S, a methoxy % of 10.0-24.0, hydroxypropyl % of 7.0-12.0, (substitution type 2208, a moisture amount of 5% max, and a bulk density of 0.23-0.35 g/cm$^3$. The formulation was prepared as described in the preceding example.

1. Benzonatate Adsorption with Calcium Silicate (BEN-Calcium Silicate Adsorbate)

| Ingredients                       | % w/w | Qty (g) |
|-----------------------------------|-------|---------|
| Benzonatate                       | 61.5  | 320.0   |
| Calcium Silicate (ZeoPharm ® 600) | 38.5  | 200.0   |
| Total                             | 100.0 | 520.0   |

Using the ingredients in the immediately preceding table, calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approximately 7 g/minute. The benzonatate-calcium silicate adsorbate granules formed were passed through 425 micron screen. Assay showed benzonatate in an amount of 60.66 wt % based on the total weight of the adsorbate.

2. Benzonatate ER Tablet

| No. | Ingredient | % w/w | Qty/Tablet (mg) | Qty/Lot (g) |
|-----|------------|-------|-----------------|-------------|
| 1 | BEN-Calcium Silicate Adsorbate of Part 1 (Assay 60.66%) | 27.5 | 247.7 | 24.77 |
| 2 | HypromelloseCR K100LV (Methocel ® K100LV) | 10.0 | 90.0 | 9.00 |
| 3 | Microcrystalline Cellulose (Ceolus ® 711) | 15.0 | 135.0 | 13.50 |
| 4 | Lactose Anhydrous (Supertab ® 22AN) | 37.5 | 337.3 | 33.73 |
| 5 | Copovidone (Kollidon ® VA 64) | 8.0 | 72.0 | 7.20 |
| 6 | Colloidal Silicon dioxide (Aerosil ® 200) | 1.0 | 9.0 | 0.90 |
| 7 | Magnesium Stearate (Hyqual ®) | 1.0 | 9.0 | 0.90 |
|   | Total | 100.0 | 900.0 | 90.00 |

Batch Size: 100 tablets

Using the ingredients in the immediately preceding table, Items 1, 2, 3, 4 & 5 were passed through 710 micron screen and mixed in a poly bag for 10 minutes. Item 6 was passed through 600 micron screen and above blend for 2 minutes. Item 7 (following being passed through a 600 micron screen) was added to above blend and mixed for 2 minutes. The final blend was compressed with Tool: 0.3310"×0.7210" (Plain).

3. In-Vitro Dissolution (0.1N HCl):

In order to assess the dissolution pattern of the tablet core, in vitro dissolution profile of the tablet was performed in 0.1N HCl and assessed at 0.5, 1 and 2 hours, using the following dissolution parameters App (II) Paddle, 50 rpm. The release percentages provided below are an average of four dissolution vessels.

| Time       | 0.5 | 1  | 3   |
|------------|-----|----|-----|
| % Released | 14  | 22 | 101 |

This tablet core may be coated with a reverse enteric coating and an optional seal coat.

Example 13

Benzonatate ER Tablet 150 mg Using Calcium Silicate as Adsorbent and Hydroxypropyl Cellulose as Extended Release Agent in Matrix This example uses an illustrative hydroxypropyl cellulose [LXF, Ashland Chemical] characterized by a molecular weight of 95,000, a viscosity of 75-150 mPa-S, a max moisture content of 5%, a pH of 5-7.5 in water, moles substitution 3.4-4.4, 0.2 max ash content, and particle sizes (min 85% through 600 micron screen, min 99% through 20 mesh).

Example 13A

Formulation A

1. Benzonatate Adsorption with Calcium Silicate (BEN-Calcium Silicate Adsorbate)

| No. | Ingredients | % w/w | Qty (g) |
|-----|-------------|-------|---------|
| 1 | Benzonatate | 61.5 | 320.0 |
| 2 | Calcium Silicate (ZeoPharm ® 600) | 38.5 | 200.0 |
|   | Total | 100.0 | 520.0 |

Using the ingredients in the immediately preceding table, calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approximately 7 g/minute. The benzonatate-calcium silicate adsorbate granules formed were passed through 425 micron screen and assayed as described in the preceding example.

2. Benzonatate ER Tablet

| No. | Ingredient | % w/w | Qty/Tablet (mg) | Qty/Lot (g) |
|-----|------------|-------|-----------------|-------------|
| 1 | BEN-Calcium Silicate Adsorbate of Part 1 (Assay 60.66%) | 27.5 | 247.7 | 24.77 |

-continued

| No. | Ingredient | % w/w | Qty/Tablet (mg) | Qty/Lot (g) |
|---|---|---|---|---|
| 2 | Hydroxypropyl cellulose LXF (Klucel ® LXF) | 20.0 | 180.0 | 18.00 |
| 3 | Microcrystalline Cellulose (Ceolus ® 711) | 10.0 | 90.0 | 9.00 |
| 4 | Lactose Anhydrous (Supertab ® 22AN) | 32.5 | 292.3 | 29.23 |
| 5 | Copovidone (Kollidon ® VA 64) | 8.0 | 72.0 | 7.20 |
| 6 | Aerosil ® 200 amorphous anhydrous colloidal silicon dioxide with a specific surface area of 200 m²/g [Evonik] | 1.0 | 9.0 | 0.90 |
| 7 | Magnesium Stearate | 1.0 | 9.0 | 0.90 |
|   | Total | 100.0 | 900.0 | 90.00 |

Batch Size: 100 tablets

Using the ingredients and amounts in the preceding table, Items 1, 2, 3, 4 & 5 were passed through 710 micron screen and mixed in a poly bag for 10 minutes. Item 6 was passed through 600 micron screen and above blend for 2 minutes. Item 7 (600 micron screen) was added to above blend and mixed for 2 minutes. The blend was compressed with Tool: 0.3310"×0.7210" (Plain) Hardness: 11 Kp.

3. In-Vitro Dissolution (0.1N HCl):

In order to assess the dissolution pattern of the tablet core, in vitro dissolution profile of the tablet was performed in 0.1N HCl and assessed at the time points shown, using the following dissolution parameters App (II) Paddle, 50 rpm. The release percentages provided below are an average of four dissolution vessels.

| Time (h) | 0.5 | 1 | 3 | 6 |
|---|---|---|---|---|
| % Released | 9 | 14 | 51 | 96 |

This tablet core may be coated with a reverse enteric coating and an optional seal coat.

Example 13B

Formulation B

1. Benzonatate Adsorption with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm ® 600) | 38.5 | 200.0 |
| Total | 100.0 | 520.0 |

Using the ingredients in the immediately, preceding table, calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approximately 7 g/minute. The benzonatate-calcium silicate adsorbate granules formed were passed through 425 micron screen.

2. Benzonatate ER Tablet

| No. | Ingredient | % w/w | Qty/Tablet (mg) | Qty/Lot (g) |
|---|---|---|---|---|
|   | Intragranular |   |   |   |
| 1 | BEN-Calcium Silicate adsorbate according to Example 13B, Part 1. (Assay 60.66%) | 27.5 | 247.7 | 24.77 |
| 2 | Hydroxypropyl cellulose LXF (Klucel ® LXF) | 20.0 | 180.0 | 18.00 |
| 3 | Microcrystalline Cellulose (Ceolus ® 711) | 10.0 | 90.0 | 9.00 |
| 4 | Lactose Anhydrous (Supertab ® 22AN) | 32.5 | 292.3 | 29.23 |
| 5 | Copovidone (Kollidon ® VA 64) | 8.0 | 72.0 | 7.20 |
| 6 | Magnesium Stearate | 0.5 | 4.5 | 0.45 |
|   | Extragranular |   |   |   |
| 7 | Aerosil ® 200 | 1.0 | 9.0 | 0.90 |
| 8 | Magnesium Stearate | 0.5 | 4.5 | 0.45 |
|   | Total | 100.0 | 900.0 | 90.00 |

Batch Size: 100 tablets

Using the ingredients in the immediately preceding table, Items 1, 2, 3, 4 & 5 were passed through 710 micron screen and mixed in a poly bag for 10 minutes. 2. Item 6 was passed through 600 micron screen and above blend for 2 minutes. The entire blend was roller compacted using a micro roller compactor (Roll speed: 1 rpm, Screw speed: 12 rpm, Pressure: 1600 psi). The compacted sheets were milled through a Fitz mill (Screen: 0065, Speed: 1100 rpm, knife forward). The blend was again roller compacted using a micro roller compactor (Roll speed: 1 rpm, Screw speed: 12 rpm, Pressure: 1600 psi). The compacted sheets were milled through a Fitz mill (Screen: 0065, Speed: 1100 rpm, knife forward). Item 7 (600 micron screen) was added to above blend and mixed for 2 minutes. The blend was compressed with Tool: 0.3310"×0.7210" (Plain) Hardness: 11 Kp.

The in vitro dissolution of the tablet core, i.e., the tablet prepared as described in Example 13B, Part 2 prior to coating with a reverse enteric coat or seal coat, was assessed in an assay with the following media: (500 mL of 0.1N HCl for 1 hr+400 mL of Phosphate Buffer), Apparatus-2, 50 rpm:

| Time (h) | 1 | 3 | 6 | 12 |
|---|---|---|---|---|
| % Released | 16 | 24 | 43 | 76 |

3. Coating with Eudragit® EPO Ready Mix (Reverse Enteric Coat)

| No. | Ingredient | % w/w | Qty/Lot (g) |
|---|---|---|---|
| 1 | Eudragit ® EPO Ready Mix* | 15.0 | 45.00 |
| 2 | Purified Water | 85.0 | 255.00 |
|   | Total | 100.0 | 300.00 |

Total Solid content = 15%

The reverse enteric coating (Item 1 in table) was mixed in water using a high shear mixer for 30 minutes at 2300 rpm. The resulting suspension was passed through 500 micron screen and stirred continuously using a magnetic stirrer. The tablets prepared as described in Example 13B, Part2 were coated with following process parameters to reach a 10 wt % reverse enteric coating level (based on the weight of the tablet prior to any seal coat). Process parameters: Inlet Temperature: 35° C., Exhaust Temp: 28° C.-30° C., Air flow: 65 cfm, Spray rate: 1.5 g/min. The coated tablets were pan dried at 40° C. for 30 minutes.

The in vitro dissolution of the reverse enteric coated tablet was assessed in an assay with the following media: (500 mL of 0.1N HCl for 1 hr+400 mL of Phosphate Buffer), Apparatus-2, 50 rpm:

| Time (h) | 1 | 3 | 6 | 12 |
|---|---|---|---|---|
| % Released | 15 | 23 | 54 | 84 |

4. Coating with Opadry® YS-1-19025-A (Seal Coat)

| No. | Ingredient | % w/w | Qty/Lot (g) |
|---|---|---|---|
| 1 | Opadry® YS-1-19025-A clear | 7.5 | 22.50 |
| 2 | Purified Water | 92.5 | 277.50 |
|  | Total | 100.0 | 300.00 |

A clear seal coat solution was prepared by adding Item 1 (Opadry® YS-1-19025-A) to Item 2 (water) and mixing for 60 minutes using an Arrow mixer. The seal coat solution was applied to the reverse enteric coated tablets prepared as described in Example 13B, Part 3, with the following parameters to reach 3 wt % seal coat level (based on the total weight of the coated tablet). Process parameters: Inlet Temperature: 60° C.-65° C., Exhaust Temp: 38° C.-48° C., Air flow: 63 cfm, Spray rate: 1.5 g/min.

The in vitro dissolution of the reverse enteric coated tablet was assessed in an assay with the following media: (500 mL of 0.1N HCl for 1 hr+400 mL of Phosphate Buffer), Apparatus-2, 50 rpm:

| Time (h) | 1 | 3 | 6 | 12 |
|---|---|---|---|---|
| % Released | 16 | 24 | 48 | 90 |

Example 14

Benzonatate ER Tablet 150 mg Using Calcium Silicate as Adsorbent and Combination of Glyceryl Behenate-Hydrophilic Polymer as Extended Release Agent in Matrix 1. Benzonatate Complexation with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm® 600) | 38.5 | 200.0 |
| Total | 100.0 | 520.0 |

Calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approximately 7 g/minute. The benzonatate-calcium silicate adsorbate granules formed were passed through 425 micron screen and assayed as described above for benzonatate content.

2. Benzonatate ER Tablet

| No. | Ingredient | % w/w | Qty/Tablet (mg) | Qty/Lot (g) |
|---|---|---|---|---|
| Intragranular |||||
| 1 | BEN-Calcium Silicate Adsorbate of Part 1 (Assay 60.66%) | 27.5 | 247.7 | 99.08 |
| 2 | Lactose Monohydrate, NF (Flow Lac® 100) | 13.3 | 119.8 | 47.92 |
| 3 | Microcrystalline Cellulose (Ceolus® 711) | 15.0 | 135.0 | 54.00 |
| 4 | Glyceryl Behenate (Compritol® 888 ATO) | 10.0 | 90.0 | 36.00 |
| Extragranular |||||
| 5 | Hypromellose E5 LV® | 5.0 | 45.0 | 18.00 |
| 6 | Calcium Silicate (ZeoPharm® 600) | 5.6 | 50.0 | 20.00 |
| 7 | Microcrystalline Cellulose (Ceolus® 711) | 7.2 | 65.0 | 26.00 |
| 8 | Lactose Monohydrate, NF (Flow Lac® 100) | 5.6 | 50.0 | 20.00 |
| 9 | Copovidone (Kollidon® VA 64) | 8.3 | 75.0 | 30.00 |
| 10 | Colloidal Silicon dioxide (Aerosil® 200) | 1.0 | 9.0 | 3.60 |
| 11 | Magnesium Stearate (Hyqual®) | 1.5 | 13.5 | 5.40 |
|  | Total | 100.0 | 900.0 | 360.00 |

Batch Size: 100 tablets

Using the ingredients and amounts in the preceding table, Items 1, 2, 3 & 4 were mixed in high shear granulator for 10 minutes (Imp: 250 rpm, Chopper: 3200 rpm). Jacketed heat was turned on and the blend was allowed to mix till the temperature reached 80° C. The blend was mixed for 10 minutes at 80° C. The blend was spread out in stainless steel trays and cooled for 2 hours. The blend was passed through 710 micron screen. Items 5, 6, 7, 8 were passed through 710 micron screen and mixed with the above blend for 10 minutes. Item 9 was passed through 600 micron screen and mixed with the above blend for 5 minutes. Item 10 was passed through 600 micron screen and 50% of it mixed with the above blend for 3 minutes. The blend was passed through a roller compactor (roll speed 1 rpm; pressure: 500 psi; screw speed 12 rpm). The ribbons were milled through Fitz Mill (Speed: 2300 rpm, Knife forward, 0050 screen). The remaining 50% of Item 10 was added to above blend and mixed for 3 minutes. The blend was compressed with Tool: 0.3600"×0.7480" (Plain); Hardness: 7 Kp.

3. Coating with Eudragit® EPO Ready Mix (Reverse Enteric Coat)

| Ingredient | % w/w | Qty/Lot (g) |
|---|---|---|
| Eudragit® EPO Ready Mix* | 15.0 | 45.00 |
| Purified Water | 85.0 | 255.00 |
| Total | 100.0 | 300.00 |

*EUDRAGIT EPO Ready Mix® is a cationic copolymer based on dimethylaminoethyl methacrylate, butyl methacrylate and methyl methacrylate. Eudragit EPO ready Mix consists of basic Butylated methacrylate copolymer, sodium lauryl sulphate, stearic acid and talc Total Solid content = 15%

The reverse enteric coating shown in the preceding table was mixed in water using a high shear mixer for 30 minutes at 2300 rpm. The suspension was passed through a 500 micron screen and stirred continuously using a magnetic stirrer. The prepared tablets were coated with following process parameters and sampled out at 10% solid content level. The process parameters were as follows: Inlet Temperature: 35° C., Exhaust Temp: 28° C.-30° C., Air flow: 65 cfm, Spray rate: 1.5 g/min. The coated tablets were pan dried at 40° C. for 30 minutes.

4. Coating with Opadry® YS-1-19025-A Seal Coat

| No. | Ingredient | % w/w | Qty/Lot (g) |
|---|---|---|---|
| 1 | Opadry YS-1-19025-A clear seal coat (hypromellose) | 7.5 | 22.50 |
| 2 | Purified Water | 92.5 | 277.50 |
|  | Total | 100.0 | 300.00 |

Total Solid content = 7.5%

Opadry YS-1-19025-A clear solution was prepared by adding Item 1 to Item 2 and mixed for 60 minutes using an Arrow mixer. Coating was performed on the reverse enteric coated tablets with following parameters and sampled out at 3% solid content level.

The process parameters were as follows: Inlet Temperature: 60° C.-65° C., Exhaust Temp: 38° C.-48° C., Air flow: 63 cfm, Spray rate: 1.5 g/min.

5. In-Vitro Dissolution (500 mL of 0.1N HCl for 1 hr+400 mL of Phosphate Buffer):

In vitro dissolution was assayed according to the assay parameters described in Example 7.

| Time (h) | 0.5 | 1 | 3 | 6 | 12 |
|---|---|---|---|---|---|
| % Released | 11 | 20 | 46 | 89 | 99 |

Example 15

Benzonatate ER Tablet 150 mg Using Calcium Silicate as Adsorbent and Combination of Hypromellose and Hydroxypropyl Cellulose as Extended Release Agent in Matrix This example illustrates blending a benzonatate-calcium silicate adsorbate with a combination of hypromellose and hydroxypropyl cellulose (HPC). The illustrated HPC is characterized by: a viscosity of 300-600 mPa-S, a molecular weight of 80 kDa, an average particle size of about 99.9% min (U.S. 60 mesh), 90% min (U.S. 80 mesh), and 80% (100 mesh). The hypromellose has a viscosity of 2663-4970 mPas and is described in detail in a preceding example.

1. Benzonatate Adsorption with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm ® 600) | 38.5 | 200.0 |
| Total | 100.0 | 520.0 |

Calcium silicate was mixed at slow speed in a high shear granulator (Impeller: 250 rpm and Chopper: 3200 rpm). Benzonatate was added to it at slow speed (Impeller: 250 rpm and Chopper: 3200 rpm) at a rate of approximately 7 g/minute. The granules formed were passed through 425 micron screen.

2. Benzonatate ER Tablet

| Sr # | Ingredient | % w/w | Qty/Tablet (mg) | Qty/Lot (gms) |
|---|---|---|---|---|
| 1 | BEN-Calcium Silicate Adsorbate from Part 1 (Assay 60.66%) | 27.5 | 247.7 | 24.77 |
| 2 | HPMC K4M (Methocel ® K4M) | 5.0 | 45.0 | 4.50 |
| 3 | Hydroxypropyl cellulose (HPC EXF ®) | 5.0 | 45.0 | 4.50 |
| 4 | Microcrystalline Cellulose (Ceolus ® 711) | 12.0 | 108.0 | 10.80 |
| 5 | Lactose Anhydrous (Supertab ® 22AN) | 40.5 | 364.3 | 36.43 |
| 6 | Copovidone (Kollidon ® VA 64) | 8.0 | 72.0 | 7.20 |
| 7 | Colloidal Silicon dioxide (Aerosil ® 200) | 1.0 | 9.0 | 0.90 |
| 8 | Magnesium Stearate (Hyqual ®) | 1.0 | 9.0 | 0.90 |
|  | Total | 100.0 | 900.0 | 90.00 |

Batch Size: 100 tablets

In order to prepare a tablet using the adsorbate prepared in the immediately preceding paragraph 1, pass Items 1, 2, 3, 4, 5 and 6 through 500 micron screen and mix in a poly bag for 10 minutes by hand. Pass Item 7 through a 500 micron screen and mix with the above blend for 2 minutes. Pass Item 8 through a 600 micron and mix with the above blend for 2 minutes. Compress the blend with Tool: 0.3310"×0.7210" (Plain); Hardness: 11 Kp.

The resulting tablet may thereafter be coated with a reverse enteric coat and an optional seal coat.

Example 16

Benzonatate/Chlorpheniramine ER Tablet 150 mg/4 mg Using Calcium Silicate as Adsorbent for Benzonatate and Hydroxypropyl Cellulose as Extended Release Agent in Matrix 1. Benzonatate Adsorption with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm ® 600) | 38.5 | 200.0 |
| Total | 100.0 | 520.0 |

Calcium silicate is mixed at slow speed in a high shear granulator (Impeller: 250 rpm and Chopper: 3200 rpm). Benzonatate is added to it at slow speed (Impeller: 250 rpm and Chopper: 3200 rpm) at a rate of approximately 7 g/minute. The benzonatate-calcium silicate adsorbate granules are passed through a 425 micron screen.

2. Benzonatate/Chlorpheniramine ER Tablet

| No. | Ingredient | % w/w | Qty/Tablet (mg) | Qty/Lot (g) |
|---|---|---|---|---|
| 1 | BEN-Calcium Silicate adsorbate according to Part 1 (Assay 60.66%) | 27.5 | 247.7 | 24.77 |
| 2 | Chlorpheniramine maleate | 0.45 | 4.00 | 0.40 |
| 3 | Hydroxypropyl cellulose LXF (Klucel ® LXF) | 20.0 | 180.0 | 18.00 |
| 4 | Microcrystalline Cellulose (Ceolus ® 711) | 10.0 | 90.0 | 9.00 |

-continued

| No. | Ingredient | % w/w | Qty/Tablet (mg) | Qty/Lot (g) |
|---|---|---|---|---|
| 5 | Lactose Anhydrous (Supertab ® 22AN) | 32.5 | 292.3 | 29.23 |
| 6 | Copovidone (Kollidon ® VA 64) | 8.0 | 72.0 | 7.20 |
| 7 | Aerosil ® 200 | 1.0 | 9.0 | 0.90 |
| 8 | Magnesium Stearate | 1.0 | 9.0 | 0.90 |
|  | Total | 100.0 | 900.0 | 90.00 |

Batch Size: 100 tablets

Items 1, 2, 3, 4, 5 & 6 are passed through a 710 micron screen and are mixed in a poly bag for 10 minutes. Item 7 is passed through a 600 micron screen, then added to above blend which is mixed for 2 minutes. Item 8 (600 micron screen) is added to above blend and is mixed for 2 minutes. The blend is compressed with Tool: 0.3310"×0.7210" (Plain) Hardness: 11 Kp.

3. Coating with Eudragit® EPO Ready Mix (Reverse Enteric Coat)

| No. | Ingredient | % w/w | Qty/Lot (g) |
|---|---|---|---|
| 1 | Eudragit ® EPO Ready Mix* | 15.0 | 45.00 |
| 2 | Purified Water | 85.0 | 255.00 |
|  | Total | 100.0 | 300.00 |

Total Solid content in coating solution = 15%

Mix the reverse enteric coating mix (Item 1) in water (Item 2) using a high shear mixer for 30 minutes at 2300 rpm. Pass the suspension through a 500 micron screen and stir continuously using a magnetic stirrer. Coat the prepared Tablets of Part 2 with the following process parameters and coated to 10 wt % reverse enteric coating, based on the weight of the reverse enteric coated tablet (prior to any seal coat). Process parameters: Inlet Temperature: 35° C., Exhaust Temp: 28° C.-30° C., Air flow: 65 cfm, Spray rate: 1.5 g/min. Pan dry the reverse enteric coated tablets at 40° C. for 30 minutes.

4. Coating with Opadry® YS-1-19025-A (Seal Coat)

| No. | Ingredient | % w/w | Qty/Lot (g) |
|---|---|---|---|
| 1 | Opadry ® YS-1-19025-A clear | 7.5 | 22.50 |
| 2 | Purified Water | 92.5 | 277.50 |
|  | Total | 100.0 | 300.00 |

Total Solid content in suspension = 7.5%

A clear solution of the seal coat is prepared by combining the Opadry® YS-1-19025-A (Item 1) to water (Item 2) and mixing for 60 minutes using an Arrow mixer. This solution is applied to the reverse enteric coated tablets with the following parameters and sample out at 3% w/w seal coat on the total weight of the tablet. Process parameters: Inlet Temperature: 60° C.-65° C., Exhaust Temp: 38° C.-48° C., Air flow: 63 cfm, Spray rate: 1.5 g/min Example 17

Benzonatate/Chlorpheniramine ER Tablet 150 mg/4 mg with an IR Chlorpheniramine Component Using Calcium Silicate as Adsorbent for Benzonatate and Hydroxypropyl Cellulose as Extended Release Agent in Matrix 1. Benzonatate Adsorption with Calcium Silicate (BEN-Calcium Silicate Adsorbate)

| Ingredients | % w/w | Qty (g) |
|---|---|---|
| Benzonatate | 61.5 | 320.0 |
| Calcium Silicate (ZeoPharm ® 600) | 38.5 | 200.0 |
| Total | 100.0 | 520.0 |

Calcium silicate is mixed at slow speed in a high shear granulator (Impeller: 250 rpm and Chopper: 3200 rpm). Benzonatate is added to it at slow speed (Impeller: 250 rpm and Chopper: 3200 rpm) at a rate of approximately 7 g/minute. The benzonanate-calcium silicate adsorbate granules formed were passed through 425 micron screen.

2. Chlorpheniramine IR Layer Blend

| No. | Ingredient | % w/w | Qty/Tablet (mg) | Qty/Lot (g) |
|---|---|---|---|---|
| 1 | Chlorpheniramine maleate | 1.00 | 2.00 | 0.90 |
| 2 | Microcrystalline Cellulose (Ceolus ® 711) | 10.0 | 20.0 | 9.00 |
| 3 | Lactose Anhydrous (Supertab ® 22AN) | 87.0 | 174.0 | 78.30 |
| 4 | Colloidal Silicon dioxide (Aerosil ® 200) | 1.0 | 2.0 | 0.90 |
| 5 | Magnesium Stearate (Hyqual ®) | 1.0 | 2.0 | 0.90 |
|  | Total | 100.0 | 200.0 | 90.00 |

Pass Items 1, 2 & 3 through 710 micron screen and mix in a poly bag for 10 minutes. Pass Item 4 through 600 micron screen, add to above blend and mix for 2 minutes. Add Item 5 (600 micron screen) to above blend and mix for 2 minutes.

3. Benzonatate/Chlorpheniramine ER Layer Blend

| No. | Ingredient | % w/w | Qty/Tablet (mg) | Qty/Lot (g) |
|---|---|---|---|---|
| 1 | BEN-Calcium Silicate adsorbate (Assay 60.66%) | 27.5 | 247.7 | 24.77 |
| 2 | Chlorpheniramine maleate | 0.22 | 2.00 | 0.20 |
| 3 | Hydroxypropyl cellulose LXF (Klucel ® LXF) | 20.0 | 180.0 | 18.00 |
| 4 | Microcrystalline Cellulose (Ceolus ® 711) | 10.0 | 90.0 | 9.00 |
| 5 | Lactose Anhydrous (Supertab ®22AN) | 32.5 | 292.3 | 29.23 |
| 6 | Copovidone (Kollidon ® VA 64) | 8.0 | 72.0 | 7.20 |
| 7 | Aerosil ® 200 | 1.0 | 9.0 | 0.90 |
| 8 | Magnesium Stearate | 1.0 | 9.0 | 0.90 |
|  | Total | 100.0 | 900.0 | 90.00 |

Batch Size: 100 tablets

Pass Items 1, 2, 3, 4, 5 & 6 through 710 micron screen and mix in a poly bag for 10 minutes. Pass Item 7 through 600 micron screen, add to above blend and mix for 2 minutes. Add Item 8 (600 micron screen) to above blend and mix for 2 minutes.

4. Compression Benzonatate/Chlorpheniramine Bilayer Tablet

Compress the two blends to specifications as bilayer tablets using a suitable double-layer tablet press. Compress the sustained release layer first. Tool: 0.3310"×0.7210" (Plain) Hardness: 11 Kp. Sustained release layer: 900 mg. Immediate release layer: 200 mg.

5. Coating with Eudragit® EPO Ready Mix (Reverse Enteric Coat)

| No. | Ingredient | % w/w | Qty/Lot (g) |
|-----|------------|-------|-------------|
| 1 | Eudragit ® EPO Ready Mix* | 15.0 | 45.00 |
| 2 | Purified Water | 85.0 | 255.00 |
|   | Total | 100.0 | 300.00 |

Total Solid content = 15%

Mix Item 1 in water using a high shear mixer for 30 minutes at 2300 rpm. Pass the suspension through a 500 micron screen and stir continuously using a magnetic stirrer. Tablets were coated with following process parameters to reach a 10 wt % reverse enteric coating on the tablets, based on the weight of the coated tablets (prior to any seal coating). Process parameters: Inlet Temperature: 35° C., Exhaust Temp: 28° C.-30° C., Air flow: 65 cfm, Spray rate: 1.5 g/min. Pan dry the coated tablets at 40° C. for 30 minutes.

6. Coating with Opadry® YS-1-19025-A (Seal Coat)

| No. | Ingredient | % w/w | Qty/Lot (g) |
|-----|------------|-------|-------------|
| 1 | Opadry ® YS-1-19025-A clear | 7.5 | 22.50 |
| 2 | Purified Water | 92.5 | 277.50 |
|   | Total | 100.0 | 300.00 |

Total Solid content = 7.5%

Prepare a clear solution of seal coat by adding Item 1 to Item 2 and mix for 60 minutes using an Arrow mixer. Coat the reverse enteric coated tablets with following parameters to reach a 3 wt % seal coat. Process parameters: Inlet Temperature: 60° C.-65° C., Exhaust Temp: 38° C.-48° C., Air flow: 63 cfm, Spray rate: 1.5 g/min.

All patents, patent publications, and other publications listed in this specification are incorporated herein by reference. Also incorporated by reference herein are U.S. patent application Ser. No. 14/282,058, filed May 20, 2014, which is a continuation of International Patent Application No. PCT/US14/023106, filed Mar. 11, 2014, U.S. Provisional Patent Application No. 61/780,689, filed Mar. 13, 2013 and U.S. Provisional Patent Application No. 61/872,019, filed Aug. 30, 2103, the benefit of the priority of which are claimed. While the invention has been described with reference to a particularly preferred embodiment, it will be appreciated that modifications can be made without departing from the spirit of the invention. Such modifications are intended to fall within the scope of the appended claims.

The invention claimed is:

1. A modified release benzonatate solid oral composition comprising (a) a homogenous solid dispersion comprising (i) benzonatate adsorbed onto one or more of a silica, silicon dioxide or silicate to form a benzonatate adsorbate and (ii) at least one pharmaceutically acceptable modified release pH-independent, hydrophilic or hydrophobic matrix-forming substance in an amount effective to provide a modified release profile to the benzonatate, and (b) a coating over said homogenous solid dispersion, wherein there is substantially no benzonatate release from the composition in the buccal cavity, and wherein the composition provides a pharmacokinetic profile for benzonatate, based on an equivalent of about a 300 mg dose of benzonatate administered at 12 hour intervals in a 24 hour period, of one or more of: a geometric mean area under the curve $(AUC)_{inf}$ of about 110 ng-h/mL to about 170 ng-h/mL, a geometric mean maximum plasma concentration $(C_{max})$ of about 28 ng/mL to about 34 ng/mL and/or a $T_{max}$ of about 12 hours to 20 hours.

2. The modified release benzonatate composition according to claim 1, wherein the composition provides a pharmacokinetic profile for benzonatate, based on an equivalent of about a 300 mg dose of benzonatate administered at 12 hour intervals in a 24 hour period, comprising one or more of: a geometric mean $C_{max}$ of about 30 ng/mL and/or a geometric mean $AUC_{inf}$ of about 150 ng-h/mL.

3. The modified release benzonatate composition according to claim 1, wherein the composition provides a pharmacokinetic profile for benzonatate, based on an equivalent of about a 300 mg dose of benzonatate administered at 12 hour intervals in a 24 hour period, comprising one or more of: an arithmetic mean $C_{max}$ of about 30 ng/mL to about 35 ng/mL and/or an arithmetic mean $AUC_{inf}$ of about 180 ng-h/mL to about 185 ng-h/mL.

4. The modified release benzonatate composition according to claim 1, wherein no more than about 25% of the benzonatate is released within 1 hour as determined in an in vitro dissolution assay.

5. The modified release benzonatate composition according to claim 1, wherein the coating is a pH-independent coating.

6. The modified release benzonatate composition according to claim 1, wherein the coating is a reverse enteric coating.

7. The modified release benzonatate composition according to claim 6, wherein said reverse enteric coating comprises (a) a pH-dependent methyl methacrylate and diethylaminoethyl methacrylate copolymer or (b) a pH-dependent cationic copolymer based on dimethylaminoethyl methacrylate, butyl methacrylate and methyl methacrylate.

8. The modified release benzonatate composition according to claim 6, wherein said reverse enteric coating comprises a pH-dependent cationic copolymer based on dimethylaminoethyl methacrylate, butyl methacrylate and methyl methacrylate.

9. The modified release benzonatate composition according to claim 6, wherein said reverse enteric coating comprises about 5% to about 40% weight of the composition.

10. The modified release benzonatate composition according to claim 1, wherein the weight ratio of benzonatate to silica, silicon dioxide, or silicate is in the range of about 5:1 to about 1:10, or about 3:1 to about 1:1.

11. The modified release benzonatate according to claim 1, wherein the benzonatate adsorbate comprises about 60% w/w benzonatate.

12. The modified release benzonatate composition according to claim 1, in which the matrix-forming substance is a hydrophilic polymer, wherein the composition comprises about 5% w/w to about 35% w/w, or about 5% w/w to about 30% w/w of the at least one hydrophilic polymer, based on the weight of the composition prior to coating.

13. The modified release benzonatate composition according to claim 12, wherein the hydrophilic polymer is a low viscosity polymer.

14. The modified release benzonatate composition according to claim 13, wherein the low viscosity, hydrophilic polymer is a hydroxypropyl methylcellulose having a viscosity of about 4000 mPa-s to about 100,000 mPa-s, or a blend of polymers containing said hydroxypropyl methylcellulose.

15. The modified release benzonatate composition according to claim 1 which is a compressed tablet.

16. The modified release benzonatate composition according to claim 15, wherein the tablet further comprises at least one excipient selected from one or more of bulking agents, binders, and lubricants.

17. The modified release benzonatate composition according to claim 1, wherein the solid oral composition further comprises at least one or more additional pharmaceutically active components.

18. The modified release benzonatate composition according to claim 17, wherein said at least one or more additional active components is selected from an anti-pyretic, an analgesic, an anti-histamine, an expectorant and a decongestant.

19. The modified release benzonatate composition according to claim 17, wherein said at least one or more additional active components are independently in immediate release form, in modified release form, or both.

20. The modified release benzonatate composition according claim 18, wherein said expectorant is guaifenesin.

21. The modified release benzonatate composition according to claim 18, which comprises one or more additional active components in the matrix.

\* \* \* \* \*